United States Patent [19]

Tannenbaum et al.

[11] Patent Number: 5,155,558
[45] Date of Patent: Oct. 13, 1992

[54] METHOD AND APPARATUS FOR ANALYZING THE APPEARANCE FEATURES OF A SURFACE

[75] Inventors: Paul M. Tannenbaum, Wilmington, Del.; Michael P. Milone, Elmer, N.J.; Dennis B. Fowler, Bear, Del.

[73] Assignee: E. I. Du Pont de Nemours and Company, Wilmington, Del.

[21] Appl. No.: 587,154

[22] Filed: Sep. 19, 1990

[51] Int. Cl.⁵ .......................................... G01N 21/47
[52] U.S. Cl. ................................ 356/446; 356/124.5; 382/8; 358/106
[58] Field of Search ............. 356/446, 440, 445, 448, 356/237, 398, 359, 124, 124.5; 382/8, 53, 43, 65; 230/571, 572, 562, 563; 358/106, 107

[56] References Cited

U.S. PATENT DOCUMENTS

| | | | |
|---|---|---|---|
| H220 | 2/1987 | Vogel | 356/124.5 |
| 2,975,285 | 3/1961 | Palmer | 356/445 |
| 3,870,414 | 3/1975 | Duffy | 356/109 |
| 3,938,892 | 2/1976 | Klingman, III | 356/124 |
| 3,999,864 | 12/1976 | Mutter | 356/212 |
| 4,197,011 | 4/1980 | Hudson | 356/354 |
| 4,299,497 | 11/1981 | Komodromos | 356/448 |
| 4,334,780 | 6/1982 | Pernick | 356/359 |
| 4,465,371 | 8/1984 | Pernick | 356/237 |
| 4,527,898 | 7/1985 | Stapleton | 356/446 |
| 4,547,073 | 10/1985 | Kugimiya | 356/371 |
| 4,572,672 | 2/1986 | Orchard et al. | 356/446 |
| 4,640,620 | 2/1987 | Schmidt | 356/376 |
| 4,682,041 | 7/1987 | Egami et al. | 250/571 |
| 4,717,259 | 1/1988 | Suga | 356/446 |
| 4,718,760 | 1/1988 | Chikama | 356/237 |
| 4,792,232 | 12/1988 | Jobe et al. | 356/394 |
| 4,846,578 | 7/1989 | Morita et al. | 356/446 |
| 4,853,777 | 8/1989 | Hupp | 358/107 |

OTHER PUBLICATIONS

*Development of a Gloss Tester for Paint Coatings*, Japanese Journal of Applied Physics, vol. 21, No. 1, Jan. 1982, pp. 133-136.
*Gloss Measurement on Painted Surfaces*, Japanese Journal of Applied Physics, vol. 20, No. 6, Jun. 1981, pp. 1145-1152.
*OTF-Quantitative Image Analysis*, David Smith, Electro Optical Systems Design, Dec. 1979, pp. 37-39.
*Design Consideration of a New Instrument for Determining Image Clarity of Coatings*, Misao Morita, Takashi Nakajima, Proc. Xth Intl Conf. Organic Coatings Science & Technology, Athens 1984.
*New Portable Orange Peel Meter for Paint Coatings*, Williamsburg Conference Proceedings, pp. 25-28.
*Computerized Roughness/Profile Measurements Quantify Aspects of Appearance*, Dr. Donald W. Boyd, PPG Ind. Proc. XIIth, Int'l Conf. in Organic Coating Science Technology, pp. 56-77, 1987.
*Appearance of Metallic Surfaces*, American Society for Testing and Materials, ASTM Special Technical Publication, 478, 1968, pp. 1-85.

*Primary Examiner*—Vincent P. McGraw
*Assistant Examiner*—LaCharles P. Reesee, II
*Attorney, Agent, or Firm*—Hilmar L. Fricke

[57] ABSTRACT

A method and apparatus for analyzing the appearance features of a surface with a spatially coherent beam of uniformly distributed collimated polychromatic light that is directed through a beam limiting means (or mask) and onto the surface at an acute angle of incidence. A scanned imaging detector, translatable through a sequence of focal plane positions along the optic axis between the mask and surface, measures the reflectance values associated with the scanned pixel intensities. After standardization, the scan intensity values are Fourier transformed into the spatial frequency domain to obtain an optical transfer function (OTF) and power and amplitude spectra. The visual spatial frequency response characteristic V(f) and standard psychophysical methodology is applied to mathematically determine surface appearance attributes such as orange peel, microwrinkle, cracks and crazes, distinctness of image (DOI), gloss, haze, contrast, luster, fog and texture.

26 Claims, 31 Drawing Sheets

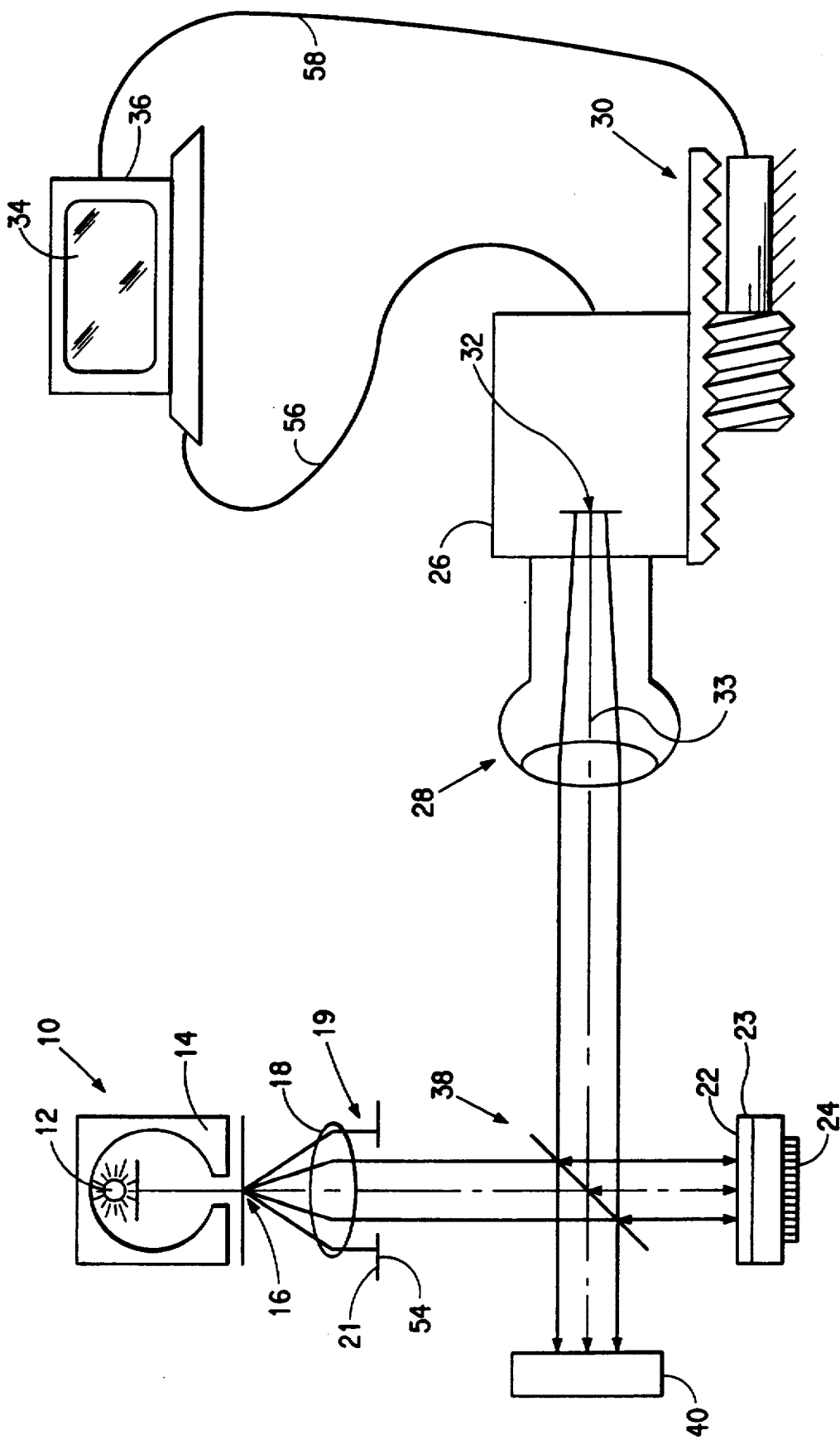

FIG.4
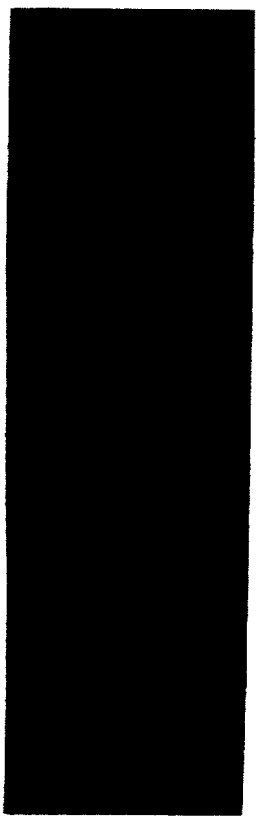

FIG. 10 TYPICAL MICROWRINKLE SCAN LINE

TYPICAL CRACKS AND CRAZES SCAN LINE

METHOD AND APPARATUS FOR ANALYZING THE APPEARANCE FEATURES OF A SURFACE

FIELD AND HISTORICAL BACKGROUND OF THE INVENTION

This invention is directed to a method of and an apparatus for analyzing the appearance features of a surface. In particular, the invention is directed to detecting the visual characteristics of a surface including orange peel, microwrinkle, cracks and crazes, distinctness of image, gloss, haze, contrast, luster, fog and texture.

Surface appearance is an essential ingredient in marketing manufactured finished products, such as paper, plastics, films, fabrics, finishes, and automobiles. For example, customers generally perceive the degree of perfection in an automotive surface finish to be indicative of the vehicle,s quality. As another example, the perception of gloss or sheen uniformity is indicative of film quality.

Various methods and devices for determining the surface characteristics have been devised in the art, and examples of same are disclosed in U.S. Pat. Nos. 2,975,285; 3,938,892; 4,299,497; 4,527,898; 4,547,073; 4,682,041; 4,717,259; 4,718,760; 4,792,232; and 4,846,578; and U.S. Statutory Invention Registration H220, published Feb. 3, 1987. Various other techniques relating to determining the characteristics of a sample surface are disclosed in the following references:

M. Morita and T. Nakajima, "Design Consideration of a New Instrument for Determining Image Clarity of Coatings", Proc. Xth Internat. Conf. in Organic Coatings Science and Technology, Athens, pp. 199-215 (1984).

M. Matsuta and T. Kubota, "Gloss Measurement on Painted Surfaces", Japanese Journal of Applied Physics, 20, pp. 1145-1152, (June 1981).

M. Matsuta, K. Kito, T. Kubota, "New Portable Orange Peel Meter for Paint Coatings", Williamsburg Conference Proceedings, pp. 25-28, Inter-Society Color Council, Williamsburg, Va., (1987).

M. Matsuta and K. Kito, "Development of a Gloss Tester for Paint Coatings", Japanese Journal of Applied Physics, 21.1, pp. 133-136 (January 1982).

Dr. Donald W. Boyd, "Computerized Roughness/-Profile Measurements Quantity Aspects of Appearance:, Proceedings of XIIIth International Conference in Organic Coatings Science and Technology, U.S.A., pp. 59-77, (1987).

"Appearance of Metallic Surfaces", ASTM Special Technical Publication 478, 71st Annual Meeting ASTM, San Francisco, Calif., (Jun. 23-28, 1968).

Various descriptors for characterizing surface appearance attributes have been standardized by the American Society of Testing and Materials (ASTM) and include such terms as orange peel (OP), distinctness of image (DOI), gloss, contrast, crazes, naze anc fog. This is not an exhaustive list since other attributes such as microwrinkle, cracks, and surface imperfections/-flaws known in the trade are also descriptive of painted surfaces. In his book, "The Measurement of Appearance", John Wiley, New York (12975), R. Hunter discusses measurement techniques for several of these attributes and stresses that the human psychophysical response to appearance is based on an interplay between measures of color and spatial vision.

In spite of the variety of instrumental methods available to us today to purportedly measure surface appearance parameters, these methods have all fallen short in their ability to fully characterize surfaces, primarily because measurements have been referenced to the surface under test rather than to the visual reference frame of the observer. Consequently, the issue of visualized detail has remained untreated. Typical of instrumentation currently in use is the non-imaging goniophotometer for measuring gloss and haze as a function of reflectance of non-collimated light at prescribed angles around the specular angle with a photocell detector.

Accordingly, the primary purpose of this invention is to provide a method and an apparatus for measuring the visual appearance attributes of surfaces that takes into account the psychophysical response of the spatial visual system, where spatial vision implies a visual capacity to detect and process image highlights, textures, and detail.

OBJECTS AND BRIEF SUMMARY OF THE INVENTION

The principal object of this invention is to provide a method and an apparatus for analyzing the appearance features of a surface, such as orange peel, microwrinkle, cracks and crazes, distinctness of image, gloss, haze, contrast, luster, fog and texture.

Another object of the present invention is to provide a method and an apparatus for analyzing the appearance features of a surface which utilizes the visual spatial frequency response characteristics and psychophysical methodology to obtain a correlation between measurement and visual assessment of the sample surface.

Another object of the present invention is to provide a method and an apparatus for analyzing the appearance features of a surface by an imaging detector which enables one to collect spatial data without the need to vary the relative angular positions of sample, source, and detector.

An additional object of the present invention is to provide a method and an apparatus for distinguishing among the various appearance attributes by isolating them in separate optical planes.

An additional object of the present invention is to provide a method and an apparatus for analyzing the appearance features of a surface which utilizes an algorithm to recognize and then focus (auto-accommodation) the image planes that contain important appearance attribute information of the surface.

Still an additional object of the present invention is to provide a method and an apparatus for analyzing the appearance features of a surface which takes into account the visual spatial frequency response of a human observer to obtain mathematical estimates of perceived visual appearance attributes of the sample surface.

A further object of this invention is to provide a method and an apparatus for analyzing the appearance features of a surface which operates by measuring reflectance as a function of spatial position.

In accordance with the above objects an appearance measurement method and apparatus has been developed to assess the visual appearance attributes of a surface, such as orange peel, microwrinkle, cracks and crazes, distinctness of image, gloss, haze, contrast, luster, fog and texture.

In the method, a collimated beam of spatially coherent white light of uniform intensity is directed through an edge object, or mask, onto a surface for reflection at the specular angle and onto the focal plane of a scanned planar array detector or camera. The scanning sensor with computer accessory detects and processes a multiplicity of image planes 10. associated with the image of surface texture, generated by the optical system, as the image plane of the detector lens tranverses the optic axis.

Surprisingly, the occurrence of specific appearance features materialize most distinctly in unique focal planes, thereby facilitating independent feature analysis. The particular focal plane position, or positions, that correspond to a given appearance attribute (or feature) is coincidentally determinable by the location of one or more peaks in the integrated Fourier power spectrum function of the scanned sequence of images that are compiled as the detector's focus passes between the edge object and the surface.

By invoking an auto-accommodation routine, the computer adjusts the camera's focal plane to those images in the sequence that correspond to integrated Fourier power spectra maximum and minimum peak positions. Scan data is then recorded for the specific appearance features that uniquely reside at those distinct focal plane positions.

After standardizing the scan measurements with the response functions of a black glass or mirror reflective surface, the spatial frequency spectra derived from the Fourier-transformed scan data and its derivatives are then combined with the achromatic visual spatial frequency response function, $V(f)$, to obtain psychophysical, mathematical characterizations of perceived visual appearance parameters.

BRIEF DESCRIPTION OF THE DRAWINGS

The above and other objects and advantages and novel features of this invention will become apparent from the following detailed description of the preferred embodiments of the invention illustrated in the accompanying drawings, in which:

FIG. 2,is an alternate embodiment of the device shown in FIG. 1;

FIG. 4 is a photographic illustration of the focal plane image of a black glass reflector;

DETAILED DESCRIPTION OF THE INVENTION

Theory

Figure 1:
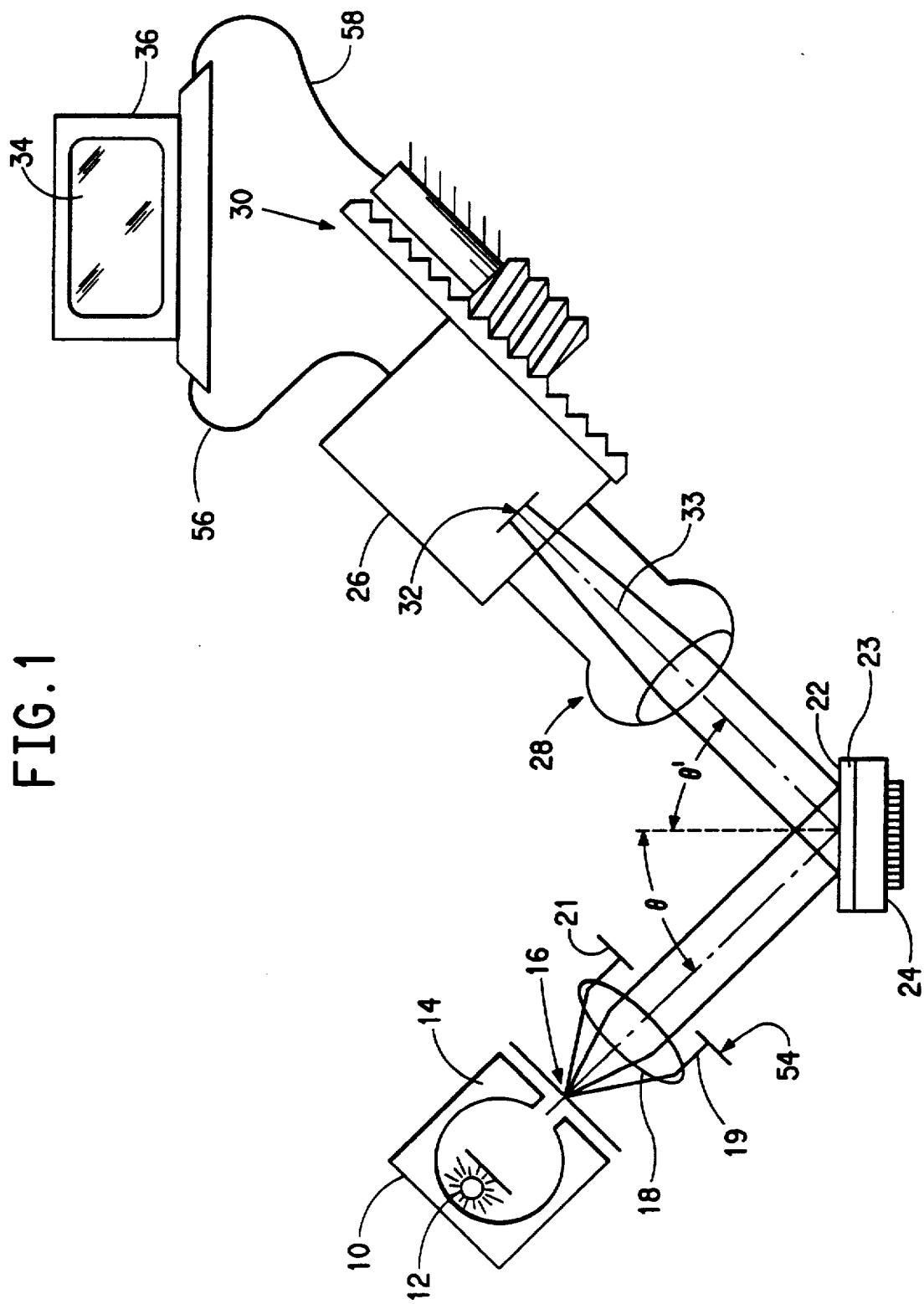
FIG. 1 is a schematic illustration showing the main components of the device of the present invention.
Figure 3A:
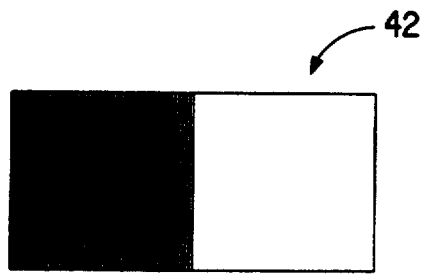
FIG. 3,is an illustration of various mask geometries that can be utilized in the present invention.
Figure 3B:
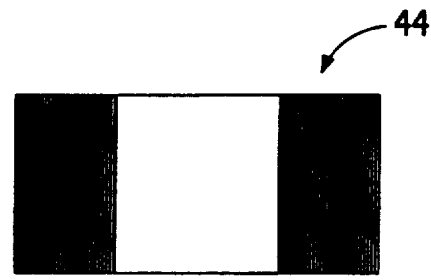
Figure 3C:
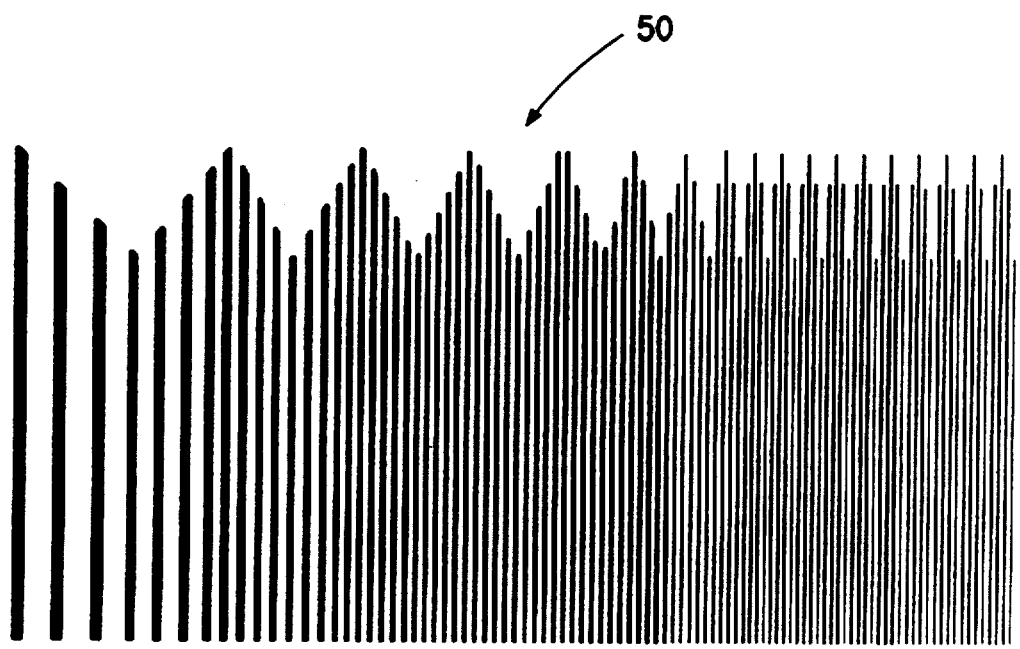
Figure 3D:
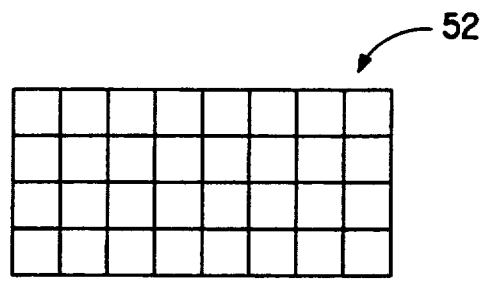
Figure 3E:
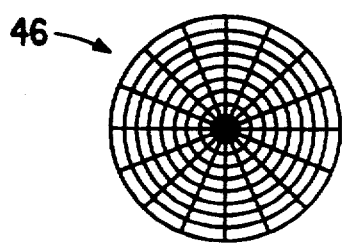
Figure 3F:
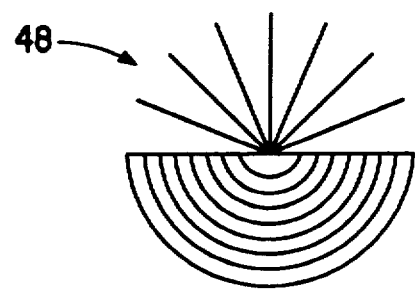
Figure 5:
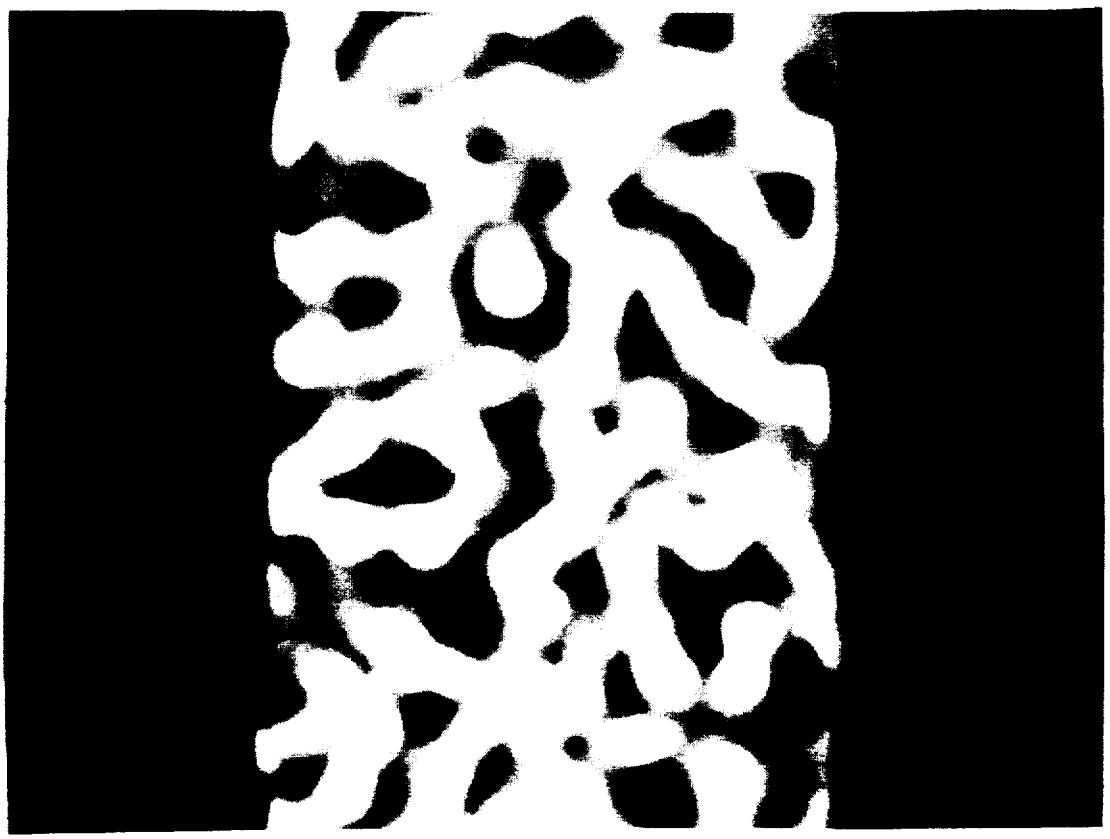
FIG. 5 is a photographic illustration of the focal plane image of typical orange peel.
Figure 6:
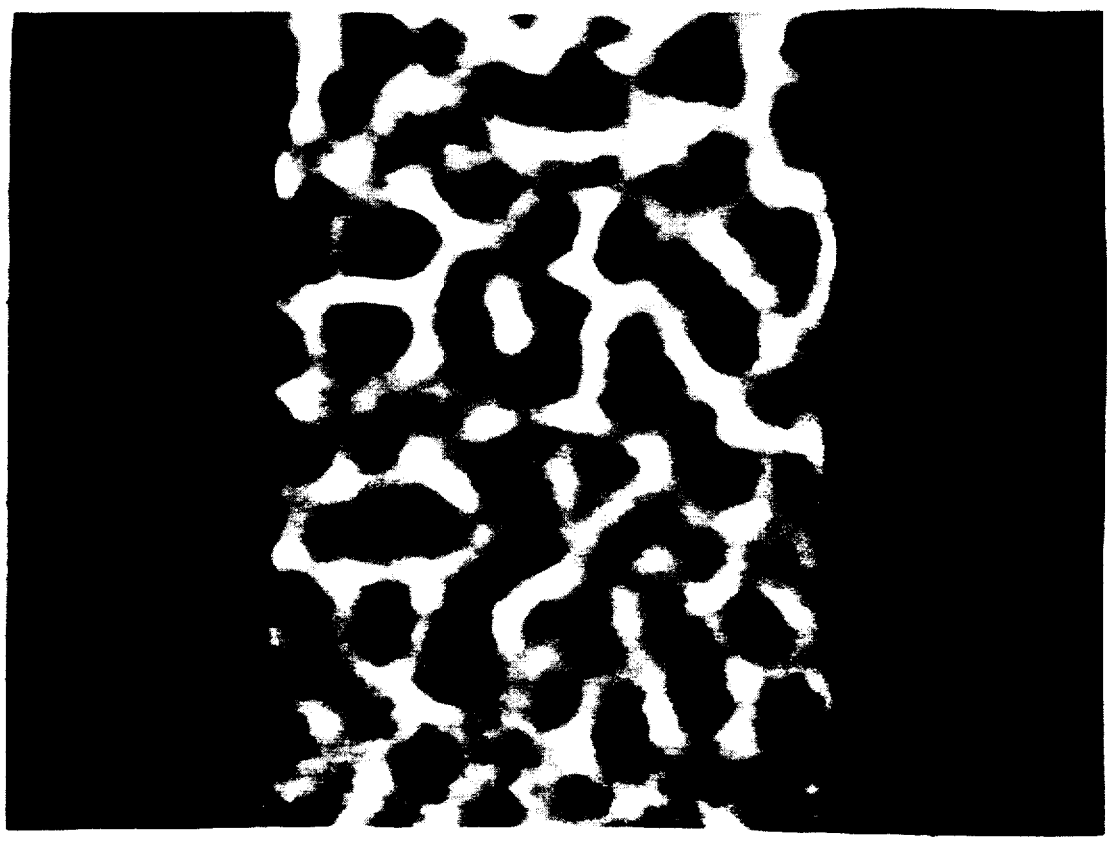
FIG. 6 is a photographic illustration of the focal plane image of typical microwrinkle.
Figure 7:
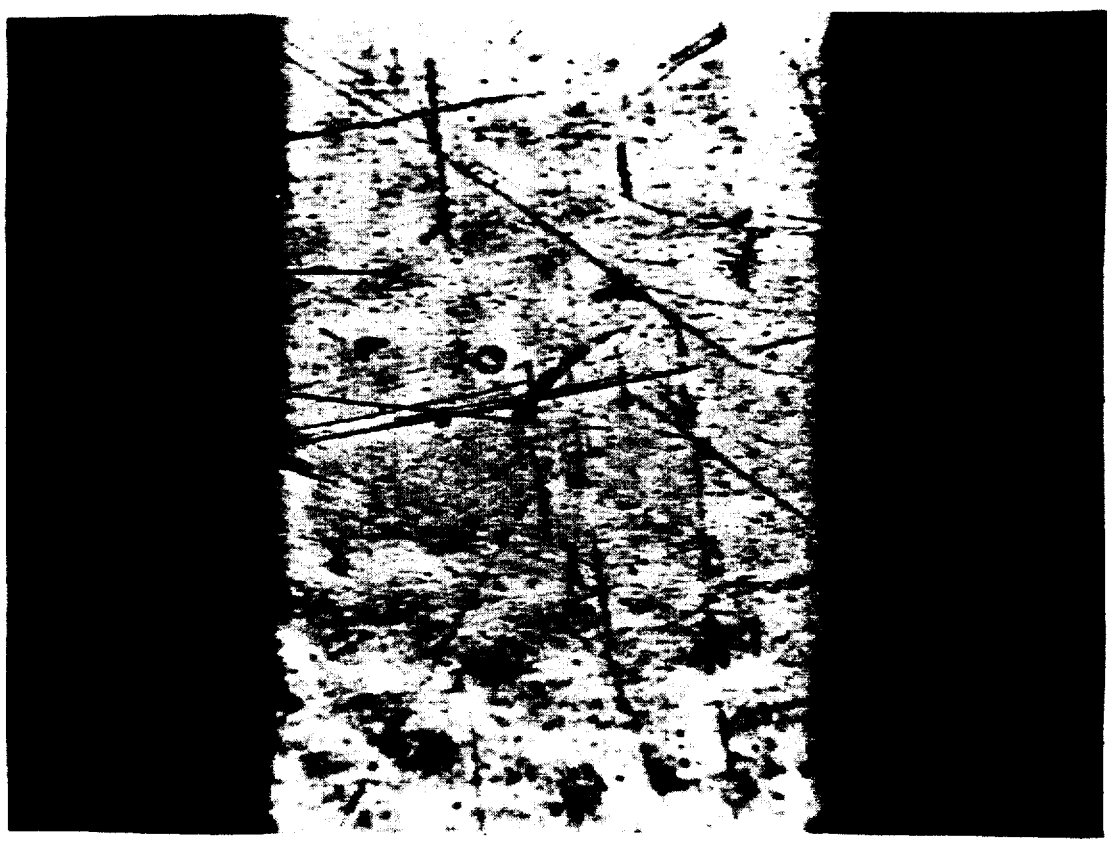
FIG. 7 is a photographic illustration of the focal plane image of typical cracks and crazes.

The science of color measurement and specification instructs us in the proper methods and techniques for assessinq surface appearance. In color, the first requirement is to measure the spectral reflectance or transmittance of the surface. This is followed by psychophysical modeling which applies the CIE standard observer Visual Response Functions: $\bar{x}_\lambda$, $\bar{y}_\lambda$, $\bar{z}_\lambda$ to compute the corresponding tristimulus values X, Y, Z, for each of the measured spectral reflectance (transmittance) values. The final phase is the perception phase which defines the subjective qualities of color; i.e., hue, saturation, lightness and color difference. In order to arrive at the latter phase, one must further transform the derived psychophysical X, Y, Z values to a perceived uniform color space based on some neurological model of color vision. The preferred model to date is the CIE (Commission International d'Eclarage), 1976 L*, a*, b* system. This invention teaches a method for applying the measurement, psychophysical, and perception modeling phases of color theory to obtain quantitative measures of visual appearance. For assessing appearance, the first requirement is to measure the surface reflectance as a function of spatial position and then to transform these results to the spatial frequency domain so that they are compatible with the achromatic visual spatial frequency response, $V(f)$, to be described below. In this invention, the measurement requirement is satisfied by Fourier-transforming each one of the sequence of scans $I^oj(x,z)$, or their derivatives $I^kj(x,z)$, taken in the image planes which are optically parallel to the target edge object. This enerates a sequence of spectra $F^kj(f,z)$ that totally characterizes the spatial frequency content of the surface under test. For a selected "y" position in the xy plane, the spectra are defined, to within a normalization constant, as:

$$F^kj(f,z) = \int I^kj(x,z) e^{ifx} dx \qquad (1),$$

where:

f represents spatial frequency k represents the derivative order ($k=o,1,\ldots$)

e represents standard notation for $\exp(x)$ z represents focal plane position x represents raster scan pixel position $I^kj(x,z)$ represents the measured intensity at raster scan position x and focal plane position z if $k=0$, and the first derivative of the measured intensity with respect to x if $k=1$ j represents the y scan index i represents the quantity $\sqrt{-1}$ The function $|F^oj(f,z)|$ is known as the amplitude spectrum of the image scan, $I^oj(x,z)$ and when an edge mask is imaged as an object through the surface, the resultant $F^1j(f,z)$ is defined as the Modulation Transfer Function (MTF) of the surface. The latter function operates in the spatial frequency domain in a manner entirely analogous to that of reflectance in the wavelength domain. In fact, there is a strict isomorphic relationship between these operations as response functions in their respective domains. Furthermore, it can be shown mathematically, that the MTF is a contrast transfer function which further enhances its utility as an appearance measure as indicated in Table 1C following.

By looking at an "average scan" or its "average derivative", generated by averaging the "x" line scans (or their derivatives) in the "y" direction, at each focal plane position "z", $$F^k(f,z) = (1/N)\Sigma F^k_j(f,z) \tag{2}$$

where N is the scan index limit (e.g. N=480), one is able to determine the degree of spatial homogeneity of $F^k(f,z)$ for a particular appearance attribute, and thus the reliability of using a single scan to characterize the surface at that focal plane position. In many instances single scan evaluations will not be sufficient and a histogram will have to be generated for each computed appearance measure derived from the family of $F^k_j(f,z)$ that includes all "x" scan lines (over y) at a given "z" position The mean, variance, height to width ratio and area under the histogram calculated for each appearance attribute can then be used as direct measures of the variation of each appearance parameter on the surface of interest.

In order to simplify the ensuing mathematical arguments we drop the subscript j with the understanding that inhomogeneous surfaces are treated with the full complement of "x" scan data.

The psychophysical modeling phase for appearance measurements is introduced by way of the isomorphic relationship between color and spatial vision. This is accomplished by applying the achromatic visual spatial frequency response function, V(f), as a weighting function to the spectral distribution functions $F^k(f,z)$ as defined by equation (2), i.e.:

$$A^k(z) = \int F^k(k,z) V(f) df \tag{3},$$

where $A^k(z)$ signifies an elementary appearance measure as seen from the "z" position of the detector. The visual response function V(f) operates in the spatial frequency domain analogously to the way the luminosity response, y, a member of the CIE Standard Observer response functions, operates in the wavelength domain. The shape of the V(f) curve corresponds, in a first approximation, to models of response data derived from numerous visual and psychophysical experiments (see for example M. L. Davidson (1966) PHD Thesis: A Perturbation Analysis of Spatial Brightness Integration in Flashed Visual Fields.) The function V(f) is similar to that of a band pass filter, with the high frequency cutoff attributed to the optics of the eye and the lower frequency cutoff attributed to spatially linked neural activity, i.e. opponent neural processing. In the vision literature, V(f) is often referred to as the visual Modulation Transfer Function (MTF), or the visual Contrast Sensitivity Function (CSF).

To achieve the final "perception stage" which determines calculated values for specific appearance attributes, the derived elementary appearance measures, $A^k(z)$, must be transformed using specified functions, $F(A^k(z))$, for each attribute. Principal determinants for the visual appearance of surfaces lie with the following "quality measures" distinctness of image, contrast, haze, gloss, orange peel, and microwrinkle. Tables 1A-1F define functions, $F(A^k(z))$, which transform the elementary appearance measures into appropriate quality measures of the specific appearance attributes enumerated above. These functions have been found to be excellent quantifiers for the above visual appearance features of test panels which transfer images to specific "z" focal plane positions.

The foregoing prescription for the calculation and quantification of appearance attributes is accomplished with the embodiments described in the next section.

THE APPARATUS

25 FIG. 1 shows the preferred embodiment of the apparatus of the invention. A white light emitting source 10 including, typically a tungsten halogen bulb 12 and located in a diffusing sphere 14, emits spatially uniform radiation via a one mm pinhole 16 to collimating lens 18.

Lens 18 forms a one cm diameter collimated beam 19 of spatially coherent and uniform light and directs it through a selected edge target object (mask) 21 and onto surface 22 of panel 23 at a fixed angle of incidence $\theta$ selected to be between 0° and 50°. Preferably, mask 21 has an aperture of about one cm². The test panel 23 is held flat, or to a limited degree of curvature, in the xy plane by means of adjustable holder 24. An imaging detector 26 with optics or lens system 28 is positioned so as to view the beam 19 along the corresponding specular angle of reflectance $\theta'$. Conventional cables 56 and 58 connect detector 26 with computer 36 and drive unit 30, respectively.

Imaging detector 26, typically a charge-coupled device (CCD) camera, is fitted with a computer controlled, worm-screw drive system 30 to sweep the imager's focal plane 32 along the "z" optic axis 33 to accommodate viewing the edge target object 21, and the various texture levels of the surface 22. Dependent upon the focal characteristic of the optics, drive system 30 moves the camera a distance of about between 0-4 inches along "z" optic axis 33. The detector 26 preferably is an area detector with about 480 active lines each including about 512 detectors. The precise locations of the attribute planes are dictated by the occurrence of the peaks and valleys in the integrated power spectra derived from the scanned images.

Although zooming the lens system 28 may be done to position the focal plane 32, translating the detector 26 and optics 28 together as a unit is preferred since it is important that the near 1:1 magnification remain unaltered. Detector camera 26 positioning may be done either manually by viewing the images on monitor 34 of computer 36 and determining the computed power spectra peak positions by eye, or by servo control loop techniques used in conjunction with accommodation algorithms of FIGS. 17 and 18. The optics 28 are designed to enable imaging of the substructure of the surfaces with characteristic dimensions of the surface variation which vary from 0.1 to 10 mm along the surface and about 1 μm perpendicular to the surface. Alternative optics can be used for other substructure dimensionalities.

FIG. 2 is an alternate embodiment of the apparatus shown in FIG. 1, in which the spatially coherent beam 19 is directed onto surface 22 at a normal angle of incidence. Viewing is also at a normal angle via beam splitter 38. This geometry may be appropriate in those cases where geometric distortion cannot be tolerated and some power loss through the beam splitter 38 would be acceptable. An optical absorber 40 is used to eliminate unwanted reflections into the lens system 28.

As illustrated in FIG. 3, the edge object target 21 may be selected from a variety of mask geometries to determine specific responses of the surface 22 to various azimuthal and spatial frequency characteristics of the input signal. Examples of masks suitable for this invention are shown where numerals 42, 44, 46, 48, 50 and 52 designate step, pulse, polar, semi-polar, Ronchi Ruling and grid masks, respectively.

Figure 8:
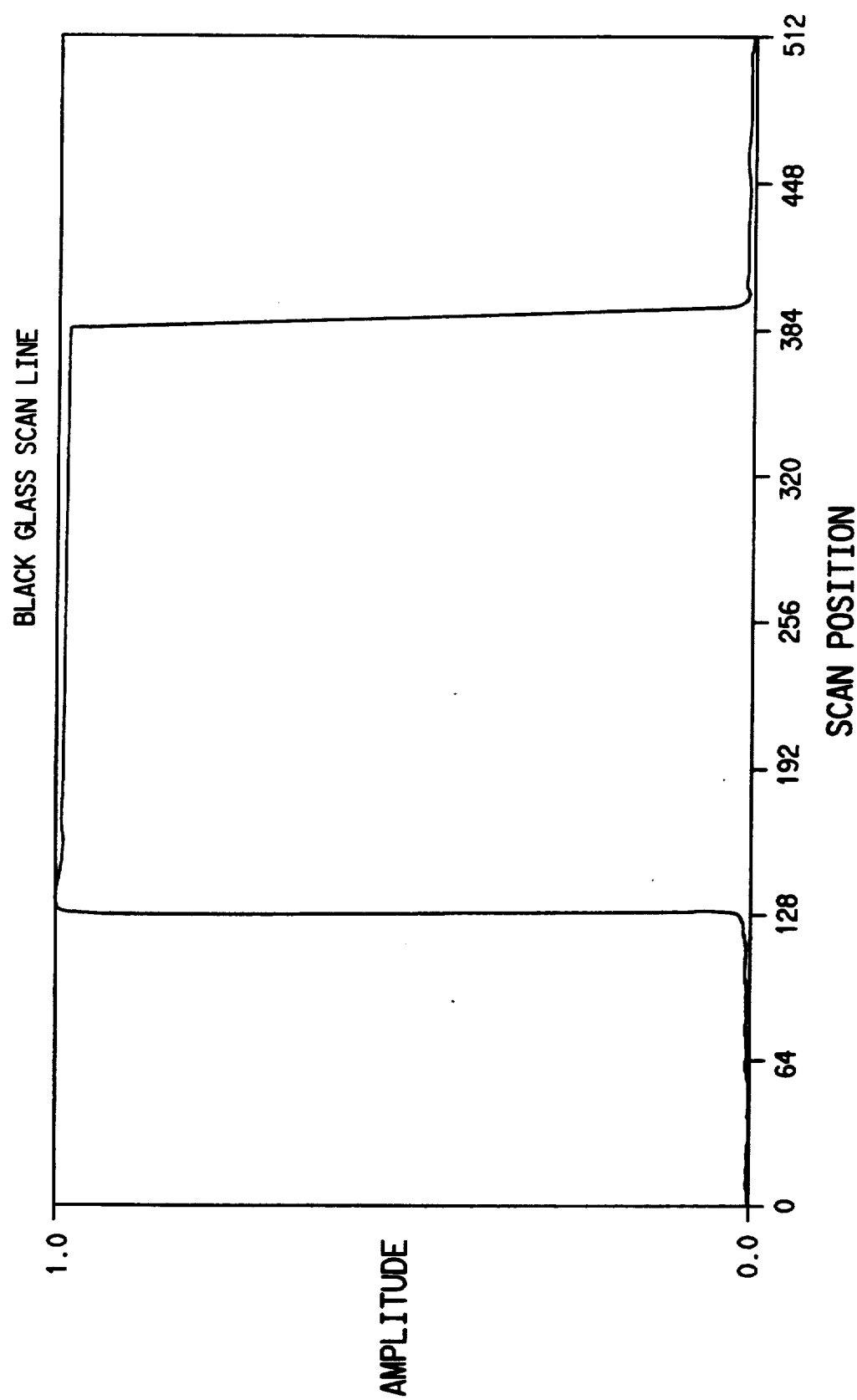
FIG. 8 is a waveform illustration of a single line scan from the image shown in FIG. 4.
Figure 9:
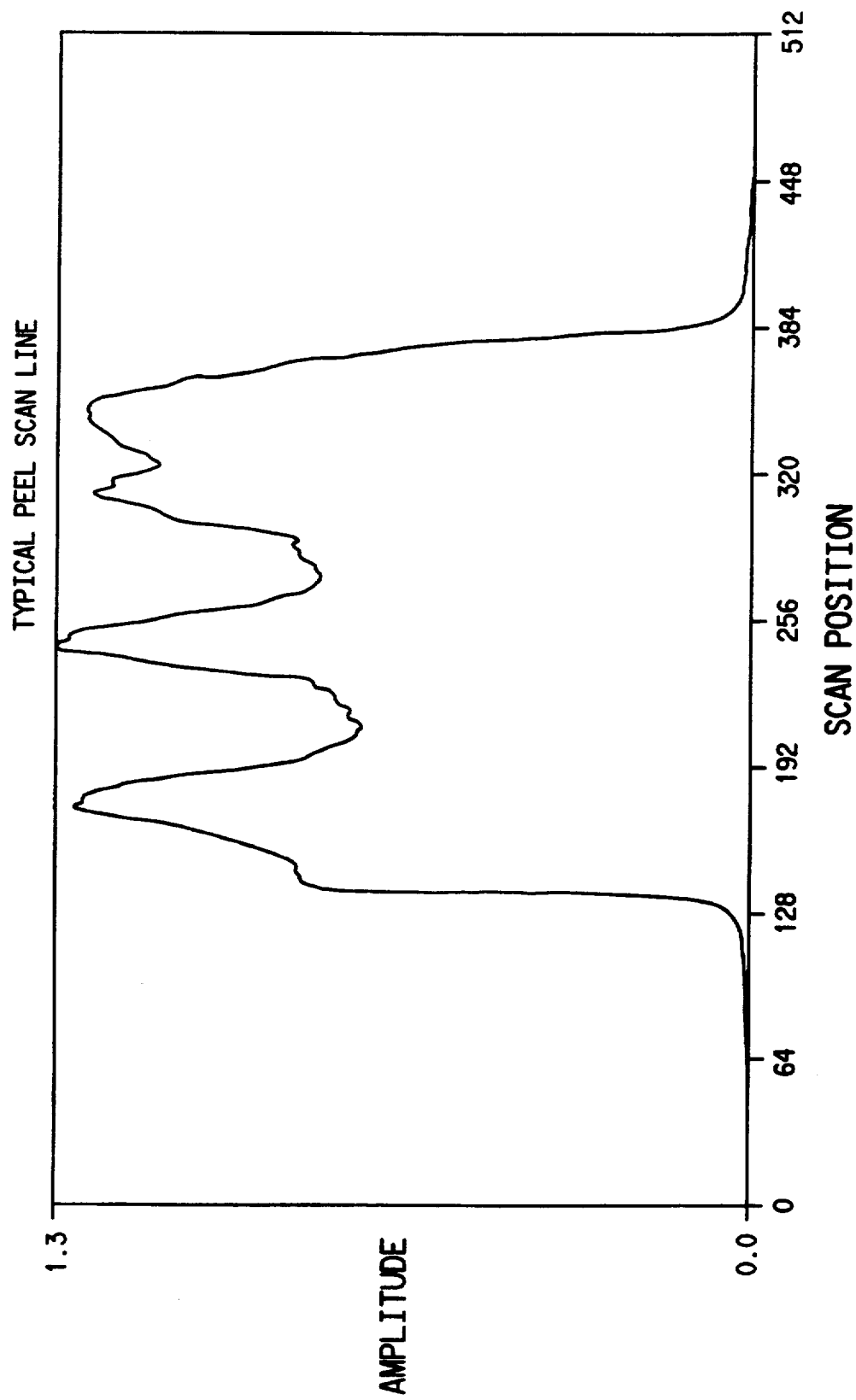
FIG. 9 is a waveform illustration of the typical peel surface image show in FIG. 5.
Figure 10:
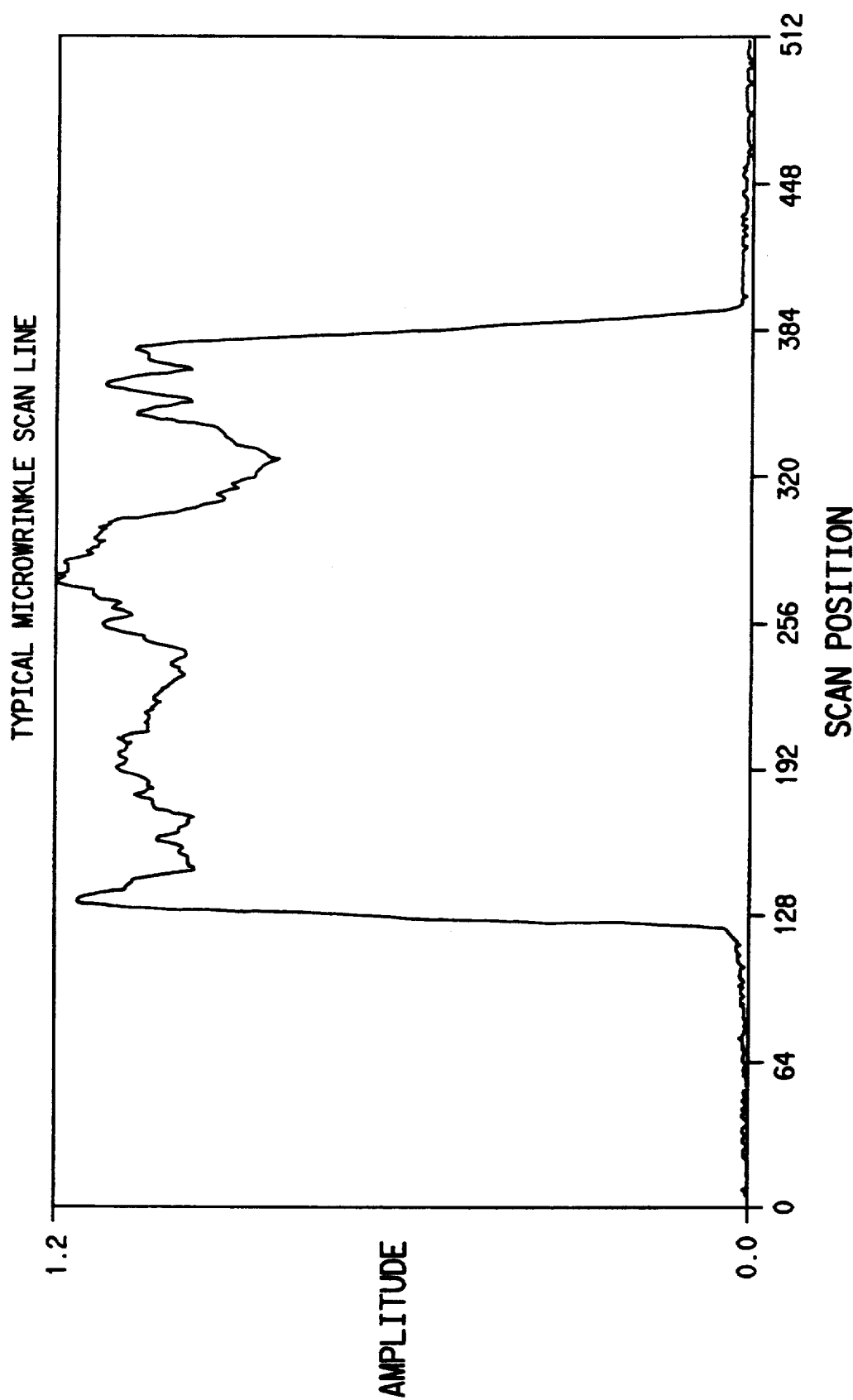
FIG. 10 is a waveform illustration of the typical microwrinkle image shown in FIG. 6.
Figure 11:
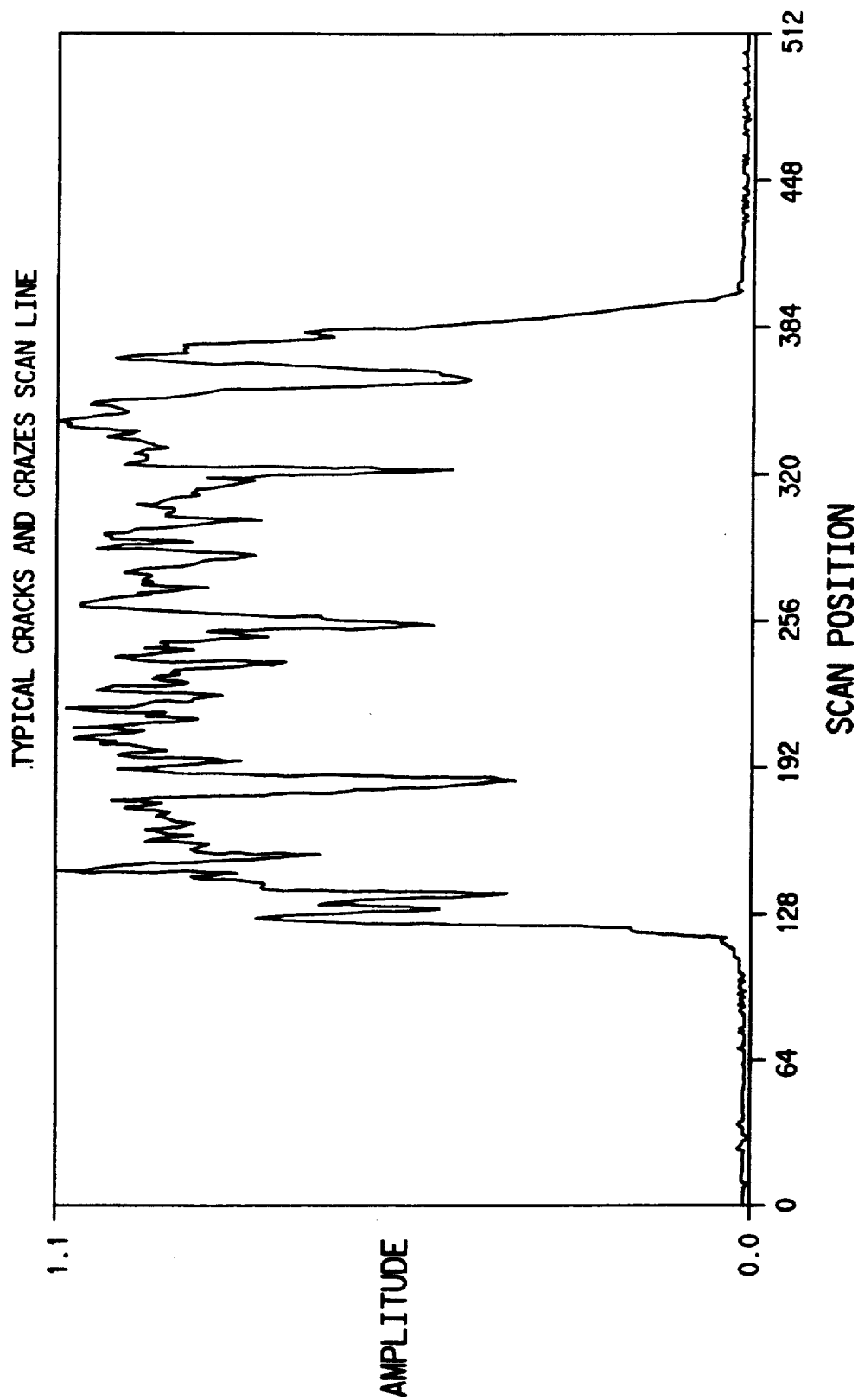
FIG. 11 is a waveform illustration of the typical cracks and crazes image shown in FIG. 7.
Figure 12:
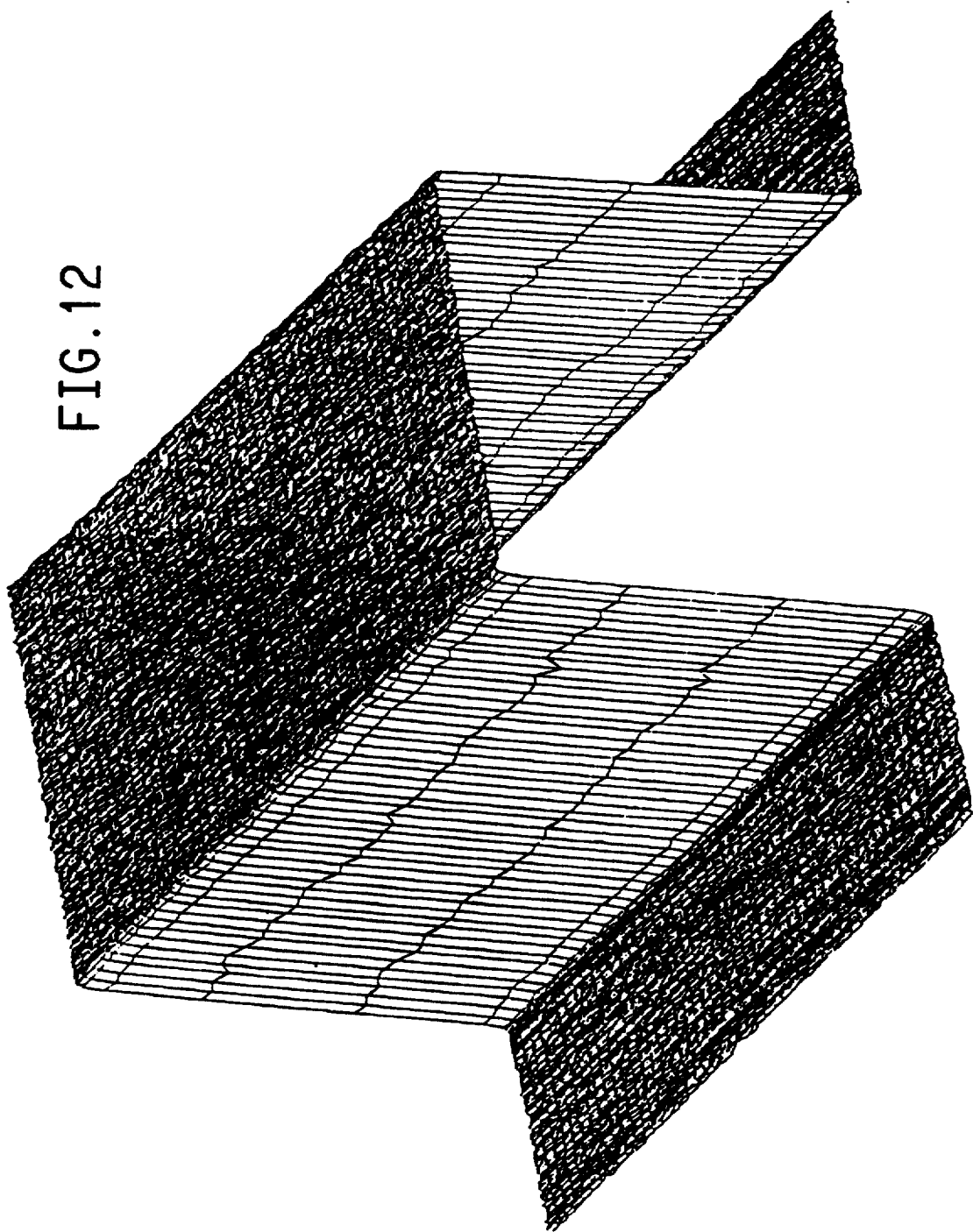
FIG. 12 is a three-dimensional representation of the data image of the black glass reflector shown in FIG. 4.
Figure 13:
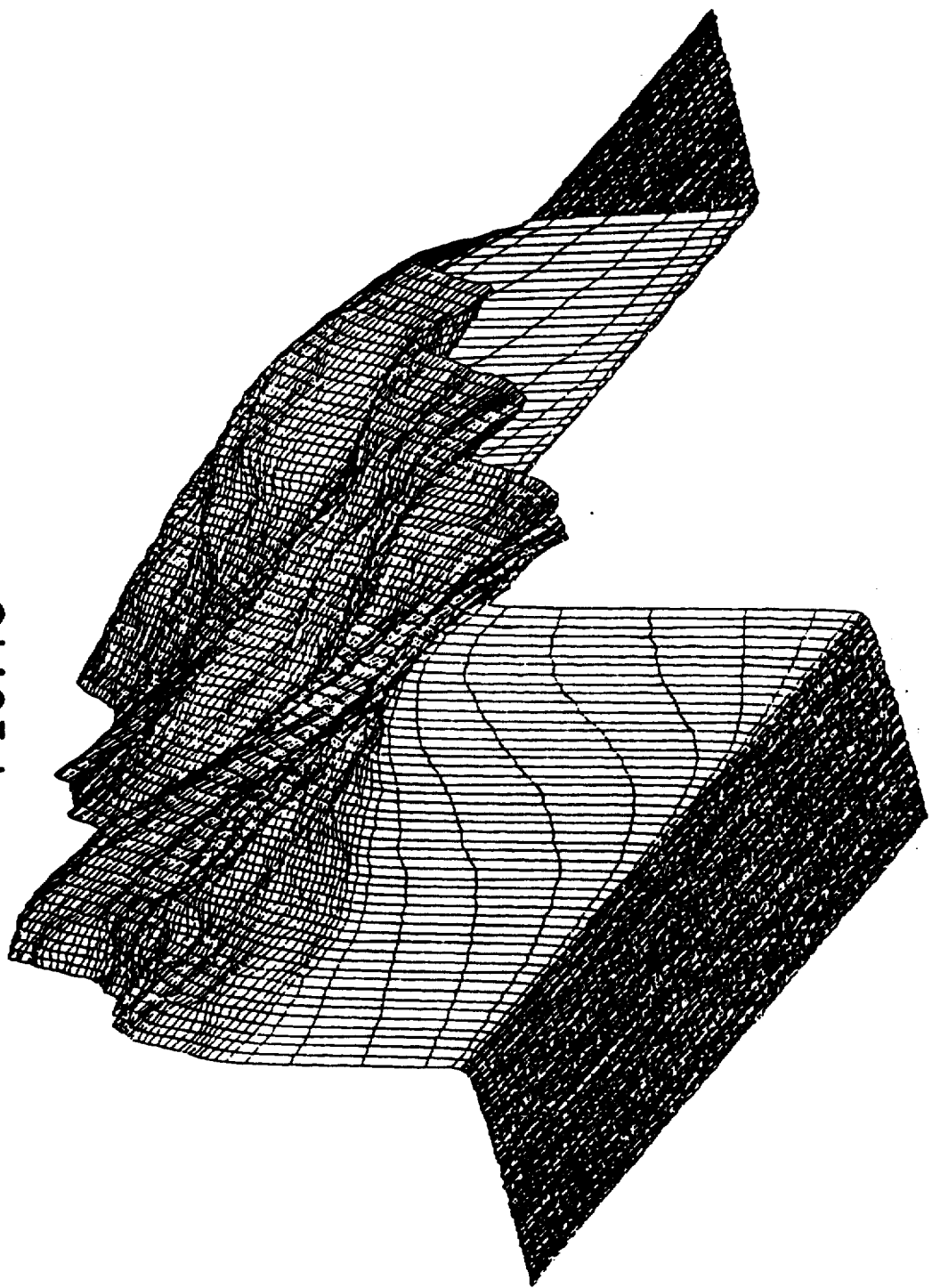
FIG. 13 is a three-dimensional representation image of typical orange peel shown in FIG. 5.
Figure 14:
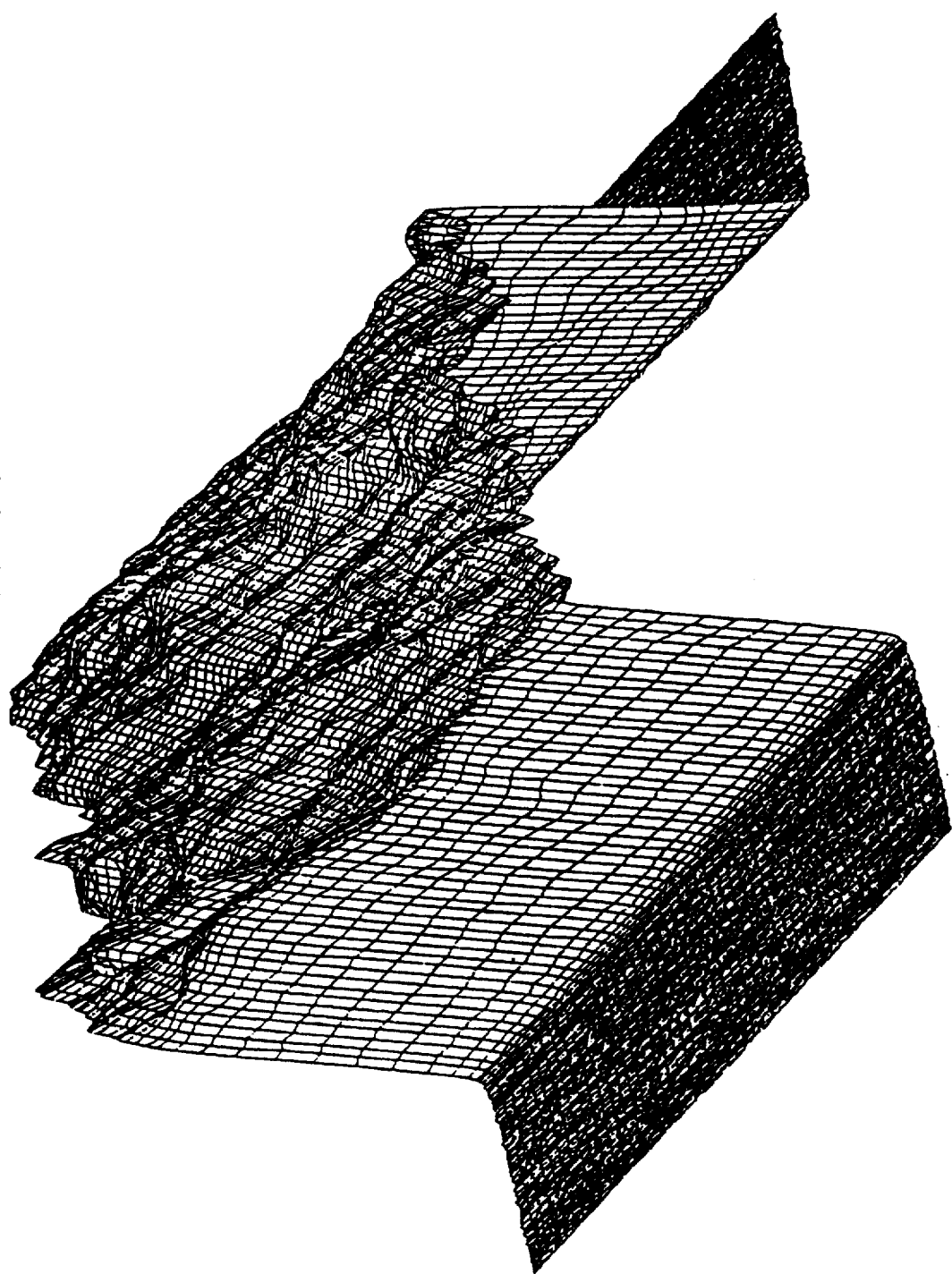
FIG. 14 is a three-dimensional representation image of typical microwrinkle shown in FIG. 6.
Figure 15:
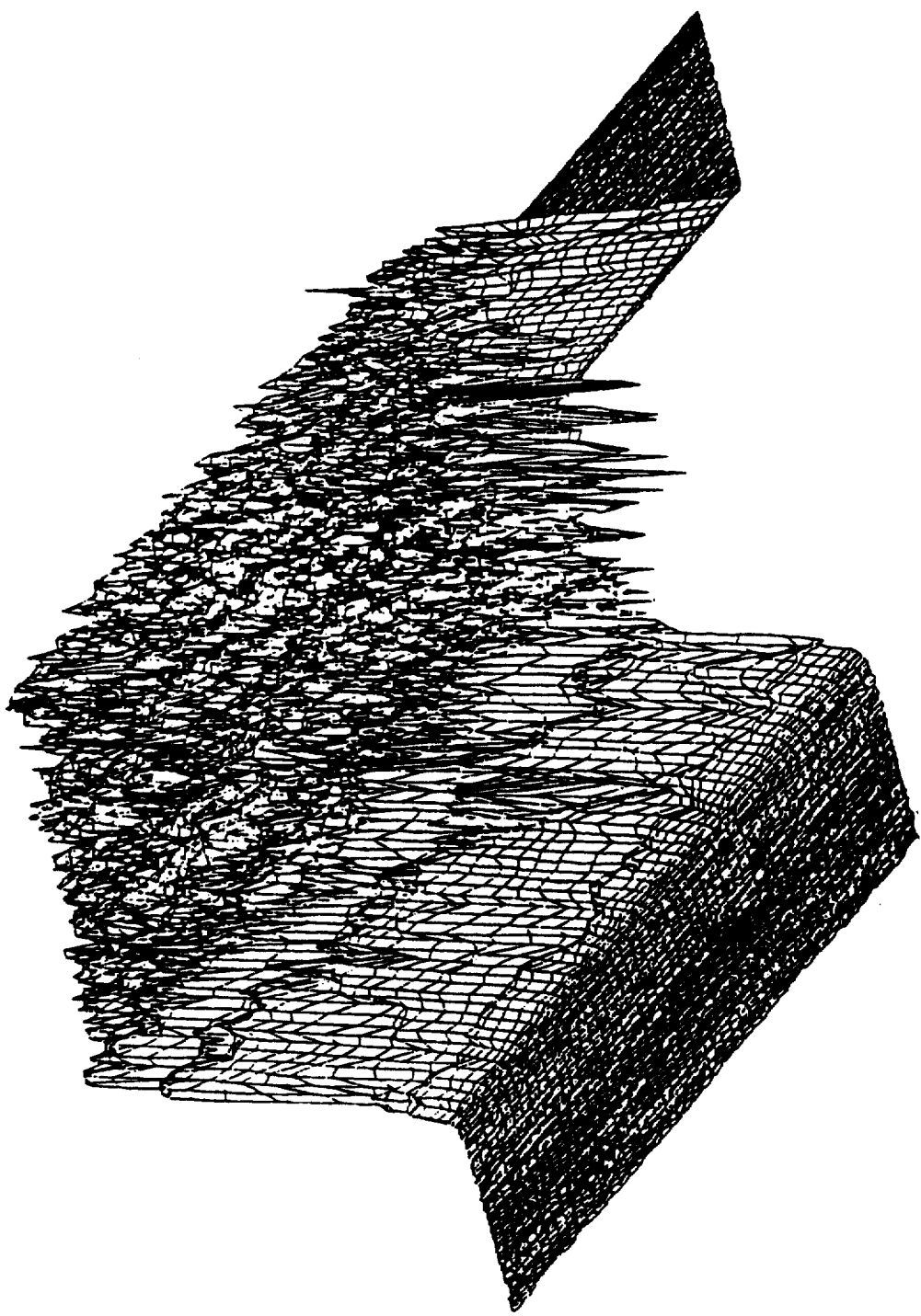
FIG. 15 is a three-dimensional representation image of typical cracks and crazes show in FIG. 7.

FIGS. 4-15 depict 3 different methods to represent the image data. FIGS. 4-7 are photographs of typical varying focal plane images normally viewed on monitor 34. FIGS. 8-11 are linear "x" waveforms of one scan line of the 480 lines which comprise the above images. FIGS. 12-15 show a 3-dimensional representation by plotting 48 of the 480 "x" waveforms in sequential "y" positions from a single image. In other words, FIGS. 4, 8, and 12 are various depictions of Black Glass reference data, FIGS. 5, 9, and 13 of typical peel data, FIGS. 6, 10, and 14 of typical microwrinkle data, and FIGS. 7, 11, and 15 of cracks and crazes data. Computer 36 can be programmed to select specific "y" and "z" scan locations and perform the various analyses needed to characterize the various surface appearance features using the procedures to be detailed next with the aid of the flow diagram of FIGS. 17-18.

THE METHOD

In order to create an image of the surface 22 that can be analyzed for texture, the beam 19 of collimated, spatially coherent and uniform polychromatic light illuminates surface 22 at a near normal angle of incidence. The imaging detector 26 builds a three-dimensional image of surface 22 when viewing at the specular angle of reflection $\theta'$. The third dimension is measured by translating the x,y focal plane of viewing detector 26 along the "z" direction optic axis 33 so as to cause the object plane 54 to pass through and image-dissect successive segments at respective equal focal plane positions through surface 22. Certain "z" displacements of detector 26 bring into focus image texture levels that are immediately identifiable by changes in the spatial frequency content of the images.

Since imaging detector 26 senses the reflection of the spatially coherent incident illumination at each point in the field of view as well as the total illumination incident upon its photosensitive surface for any given focal position, textural detail becomes apparent that would otherwise be lost if incoherent illumination were to be used.

When edge target object 21 is introduced into beam 19 at a point between the source of illumination 10 and the surface 22, contrast and DOI appearance features can be measured by changing the focus of the detector 26 from surface 22 to the image of the edge target 21 itself. Thus, the translatable imaging detector 26 is able to perform the accommodation function similar to that of the eye when focusing on near or far objects.

Each of the signal waveforms, $I^o j(x,z)$, of FIGS. 8 to 11, generated by scanning in the "z direction across successive focal plane images of surface 22 with edge target mask 21 introduced into beam 19 as shown in FIGS. 4-7, is Fourier transformed in accordance with equation (1) to obtain a series of amplitude spectra $|F^o j(f,z)|$ as functions of optic axis distance "z" with corresponding reflected power spectra $P^o j(f,z)$, where $$P^o j(f,z) = (F^o j(f,z))^* (F^o j(f,z))|^2 \qquad (4)$$

A close examination of the power spectra shows that the sharper the edge object image is, the more significant the low spatial frequency component amplitudes of $P^o j(f,z)$ become. Similarly, the high spatial frequency components are more pronounced for a sharper edge than for a less distinct edge feature as the higher frequency components are needed to define a sharp edge transition. By compressing the range of power spectra values with a log function and integrating over spatial frequencies, we derive a new function, $T_j(z)$, representing the total reflected image power (log units) as a function of position "z" along the optic axis:

$$T_j(z) = \int \log[P^o j(f,z) + 1] df \qquad (5)$$

(1 is added to the power function to make the integral positive definite). Results of this integration show that the sharper (i.e., more "in focus") images yield the larger $T_j(z)$ values. This is also observed by examining the peaks in a representative graph of $T(z)$, which is the "y" averaged value of $T_j(z)$ calculated in accordance with the prescription defined by equation (5) and shown in FIG. 16 for a set of focal positions "z" The peaks in this graph precisely identify the positions and best focus for each appearance attribute of significance associated with the surface 22. This characteristic is, therefore, the basis for the algorithm used in conjunction with servo control loop techniques known in the art and forms the basis upon which the auto-accommodation feature of the invention rests.

Figure 19A:
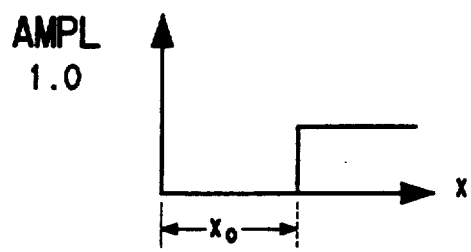

As already stated, the principal determinants for the visual appearance of surfaces lie with the following "quality measures" distinctness of image, contrast, haze, gloss, orange peel, and microwrinkle. These parameters may be defined mathematically in a number of ways using the following functions which are each, individually "ideal" representations of the measured data, $I^o j(x,z)$, for fixed "y" and "z" (i.e., $I^o j(x,z) = (H(x)$ or $S(x)$ or $P(x)$, etc.):

(a) Step Function $H(x)$:

See FIG. 19A.
obtained by scanning an edge object reflected from an ideal black glass or mirror reference with the imager's object plane at the edge target position.

Figure 19B:
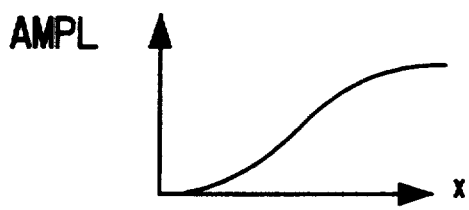

(b) Blurred Edoe Transition $S(x)$:

See FIG. 19B.
obtained by scanning the image of an edge object reflected from a poorly reflecting surface with imager's object plane at the edge target position.

Figure 19C:
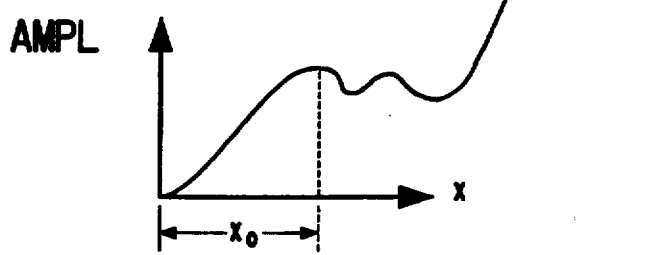

(c) Orange Peel Transition $P(x)$:

See FIG. 19C.
obtained by scanning the image of an edge object reflected from a surface with orange peel, with the object plane at the edge target position. "$x_o$" is the transition distance. Since this function contains both edge transition and residual peel components, i.e., $P(x) = S(x) + \Phi(x - x_o)$, it is necessary to separate the two components from one another before independent values of OP and DOI can be derived. One way to separate these variables, for example, is to take two sequential scan measurements in collimated and diffuse illumination at the DOI edge target focus position. By subtracting the two data sets the resultant S(x) function is obtained.

Figure 19D:
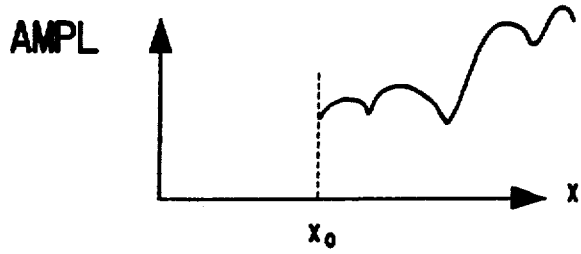

(d) Residual Peel Component $\Phi(X-X_o)$:

See FIG. 19D.

the above is obtained by subtracting S(x) from P(x), defined for $x > x_o$.

Figure 19E:
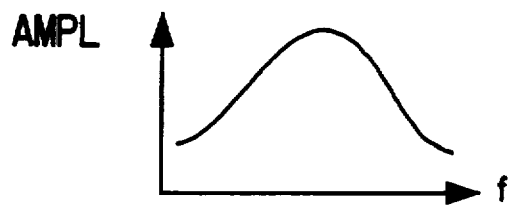

(e) Visual Spatial Frequency Response V(f):

See FIG. 19E.

the above represents the eye's response to luminance transitions as a function of spatial frequency. The V(f) function was initially defined by Davidson (1966) as a result of extensive experimentation with human subjects and has since been quantified. (R. W. Cohen, I. Gorog, C. R. Carlso, "Image Descriptors for Displays, pg. 33, March 1975, RCA Technical Report prepared for the Office of Naval Research.)

Figure 19F:

(f) Optical Transfer Function (Transition/Peel) OTF(f):

See FIG. 19F.

This is derived by taking the Fourier Transform of the line spread function, i.e., the derivative of the edge transition function S(x) or H(x) with respect to scan displacement, $x(f_c = \text{frequency at limiting resolution})$.

(g) Line Spread Function for Perfect Edge:

$$\frac{dH(x)}{dx} = \delta(x)$$

Figure 19G:
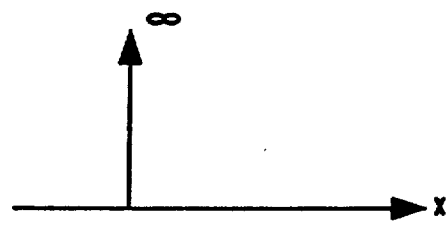

See. FIG. 19G.

The above is not readily attainable, but is closely approximated by an edge target and mirror black glass reflective surface. Since $FT\{\delta(x)\} = 1$, it is useful as a reference for standardizing DOI spectra measurements.

Figure 19H:
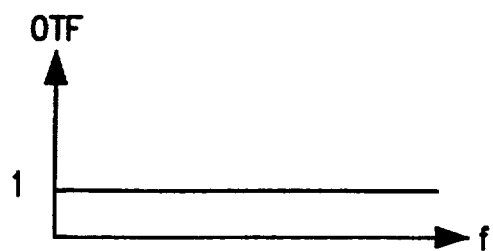

(h) Fourier Transform Pairs:

See FIG. 19H.

$F.T.\{S(x)\} =$ $$\bar{s}(f) = \int_{-\infty}^{\infty} e^{ifx}S(x)dx; \text{ to within a normalizing constant}$$

The convention is upper case for spatial variables, S(x), and lower case, $\bar{S}$ (f), for functions of frequency. The Fourier transform pair is then defined as:$[S(x), \bar{s}(f)]$ For convenience, representative equations for deriving quality measures for the principal surface visual appearance attributes are listed in Tables 1A–1F. These are all definable with data extracted and analyzed in accordance with the invention.

TABLE 1A

QUALITY MEASURES FOR DISTINCTNESS OF IMAGE (DOI)

Figure 20A:
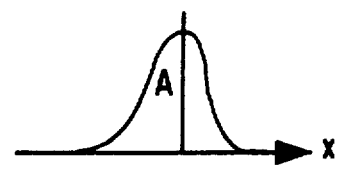
FIGS. 20$a$-$z$ are graphical representation of Quality Measures for Distinctness of Image.
Figure 20B:
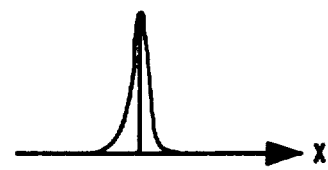
Figure 20C:
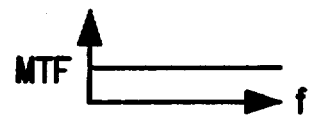
Figure 20D:
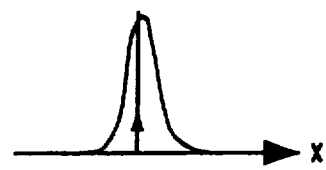
Figure 20E:
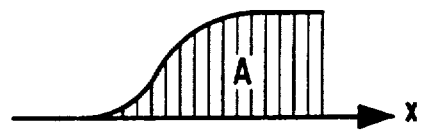
Figure 20F:
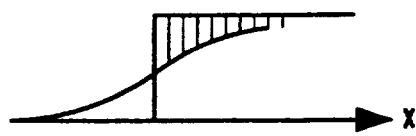
Figure 20G:
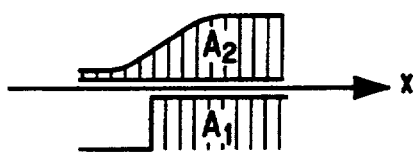
Figure 20H:
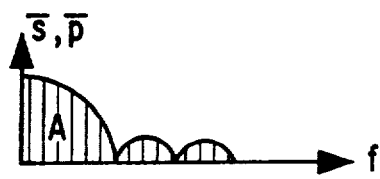
Figure 20I:
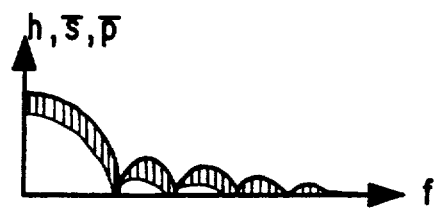

| NAME | EQUATION/OPERATION | GRAPHICAL REPRESENTATION | QUANTIFYABLE PARAMENTERS | COMMENTS |
|---|---|---|---|---|
| Line Spread Function | $\frac{dS(x)}{dx}$ | See FIG. 20A. | $h, w, \frac{h}{w}, A$ | DOI measure, used in photography as a measure of image sharpness. |
| Line Spread For a Perfect Edge | $\frac{dH(x)}{dx} = \delta(x)$ | See FIG. 20D. | $h \to \infty, w \to o$ | Reference measure; $F.T.\{\delta(x)\} = 1$; See FIG. 20C. |
| *Acutance | $\left(\frac{dS(x)}{dx}\right)^2$ | See FIG. 20D. | $h, w, \frac{h}{w}, A$ | DOI measure, also used in photography as a Quality measure. Area sometimes normalized by 1/L; L = range of integration |
| Curvature $C_u(x)$ | $\frac{d^2S(x)/dx^2}{[1 + (dS/dx)^2]^{3/2}}$ | | | DOI measure; sensitive to curvature in the "elbows" of S. |
| Spatial Area | $\int S(x)dx; \int p(x)dx$ | See FIG. 20E. | A | DOI measure (absolute) for (S); Image Quality For (P) |
| Spatial Area Difference | $\int [H(x)-S(x)]dx; \int [H(x)-P(x)]dx$ | See FIG. 20F. | $A_1 - A_2$ | DOI measure (Relative) For (S); Image Quality For (P) |
| Spatial Area Ratio | $\frac{\int S(x)dx}{\int H(x)dx}; \frac{\int P(x)dx}{\int H(x)dx}$ | See FIG. 20G. | $A_2/A_1$ | DOI Measure (Relative) For (S); Image Quality For (P) |
| Spectral Area (Amplitude) | $\int \bar{s}(f)df; \int \bar{p}(f)df$ | See FIG. 20H. | A | DOI Measure (Absolute) For (S); Image Quality For (P) |
| Spectral Area Difference (Amplitude) | $\int [h(f) - \bar{s}(f)]df; \int [h(f) - \bar{p}(f)]df$ | See FIG. 20I. | $A_1 - A_2$ | DOI Measure (Relative) For (S); Image Quality For (P) |

TABLE 1A-continued

QUALITY MEASURES FOR DISTINCTNESS OF IMAGE (DOI)

Figure 20J:
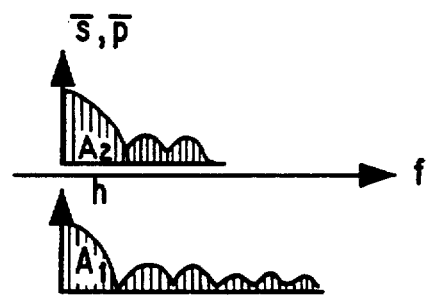
Figure 20K:
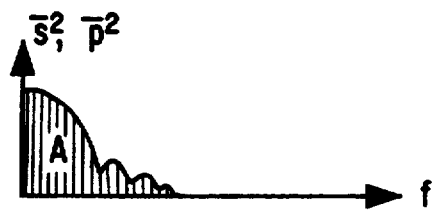
Figure 20L:
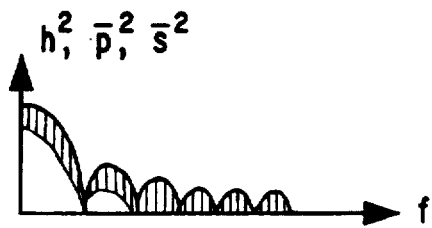
Figure 20M:
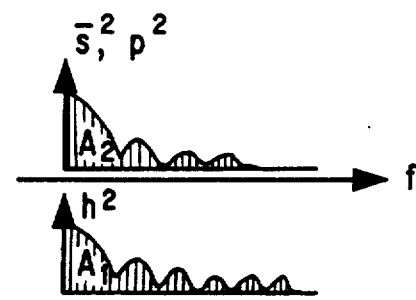
Figure 20N:
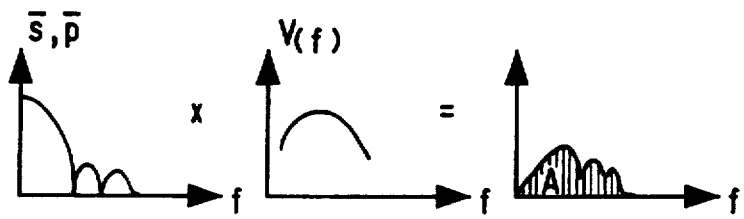
Figure 20:
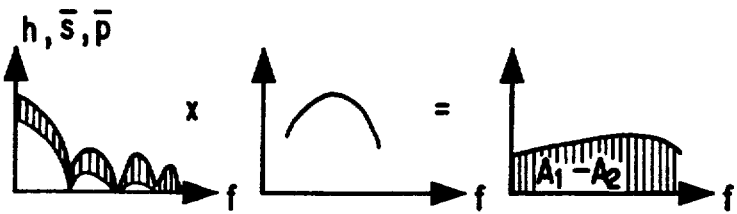
Figure 20P:
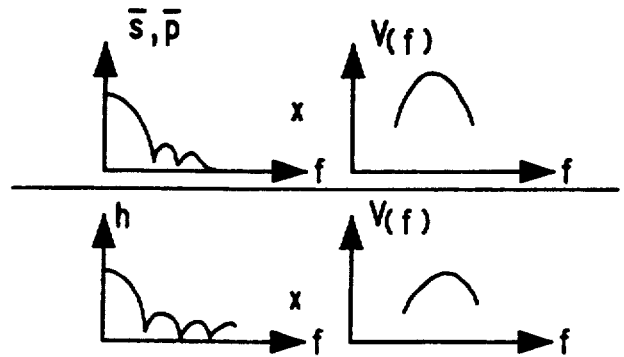
Figure 20Q:
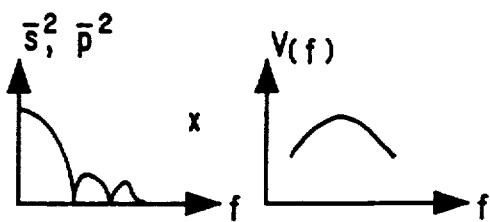
Figure 20R:
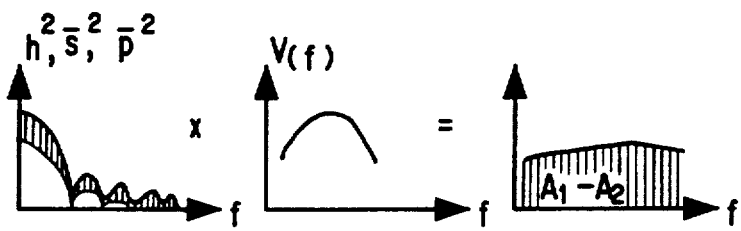
Figure 20S:
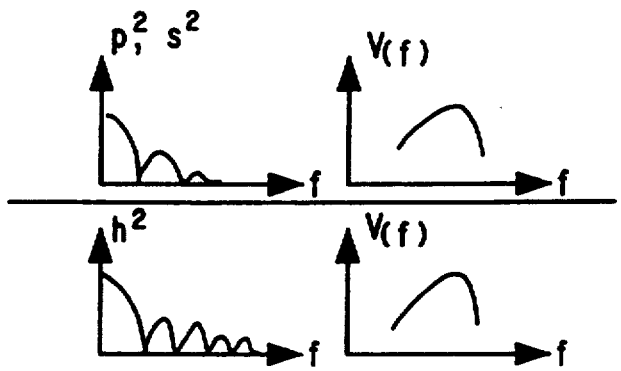

| NAME | EQUATION/OPERATION | GRAPHICAL REPRESENTATION | QUANTIFYABLE PARAMENTERS | COMMENTS |
|---|---|---|---|---|
| Spectral Area Ratio (Amplitude) | $\dfrac{\int s^-(f)df}{\int h(f)df}$ ; $\dfrac{\int p^-(f)pf}{\int h(f)df}$ | See FIG. 20J. | $A_2/A_1$ | DOI Measure For (S); Image Quality Measure For (P) |
| Spectral Area (Power) | $\int \|\bar{s}(f)\|^2 df$; $\int \|\bar{p}(f)\|^2 df$ | See FIG. 20K. | A | DOI Measure For (S); Image Quality Measure For (P) |
| Spectral Area Difference (Power) | $\int [\|h(f)\|^2 - \|\bar{s}(f)\|^2]df$ <br> $\int [\|h(f)\|^2 - \|\bar{p}(f)\|^2]df$ | See FIG. 20L. | $A_1 - A_2$ | DOI Measure For (S); Image Quality Measure For (P) |
| Spectral Area Ratio (Power) | $\dfrac{\int \|\bar{s}(f)\|^2 df}{\int \|h(f)\|^2 df}$ ; $\dfrac{\int \|\bar{p}(f)\|^2 df}{\int \|h(f)\|^2 df}$ | See FIG. M. | $A_2/A_1$ | DOI Measure For (S); Image Quality Measure For (P) |
| Visually Weighted Spectral Area (Amplitude) | $\int \bar{s}(f)V(f)df$; $\int \bar{p}(f)V(f)df$ | See FIG. N. | A | DOI Measure For (S); Image Quality Measure For (P) |
| *Visually Weighted Spectral Area Difference (Amplitude) | $\int [h(f) - \bar{s}(f)]V(f)df$ <br> $\int [h(f) - \bar{p}(f)]V(f)df$ | See FIG. 20O. | $A_1 - A_2$ | DOI Measure For (S); Image Quality Measure For (P) |
| Visually Weighted Spectral Area Ratio (Amplitude) | $\dfrac{\int s^-(f)V(f)df}{\int h(f)V(f)df}$ ; $\dfrac{\int p^-(f)V(f)df}{\int h(f)V(f)df}$ | See FIG. 20P. | $A_2/A_1$ | DOI Measure For (S); Image Quality Measure For (P) |
| Visually Weighted Spectral Area (Power) | $\int \|\bar{s}(f)\|^2 V(f)df$; <br> $\int \|\bar{p}(f)\|^2 V(f)df$ | See FIG. 20Q. | A | DOI Measure For (S); Image Quality Measure For (P) |
| Visually Weighted Spectral Area Difference (Power) | $\int [\|h(f)\|^2 - \|\bar{s}(f)\|^2]V(f)df$ <br> $\int [\|h(f)\|^2 - \|\bar{p}(f)\|^2]V(f)df$ | See FIG. 20R. | $A_1 - A_2$ | DOI Measure For (S); Image Quality Measure For (P) |
| Visually Weighted Spectral Area Ratio (Power) | $\dfrac{\int \|\bar{s}(f)\|^2 V(f)df}{\int \|h(f)\|^2 V(f)df}$ ; $\dfrac{\int \|\bar{p}(f)\|^2 V(f)df}{\int \|h(f)\|^2 V(f)df}$ | See FIG. 20S. | $A_2/A_1$ | DOI Measure For (S); Image Quality Measure For (P) |
| *Power Law Spatial Visual Response Q2 | $1/K_2 \int (h(f)OTF(f))^\gamma V(f)df$ <br> where: <br> $K_2 = \int (h(f)OTF(f)_{BG})^\gamma V(f)df$ | | $A^\gamma$ | Cornsweet claims the visual spatial response is to a non-linear stimulus. Value depends on focal plane position "z". DOI (absolute) measure and image quality measure |

TABLE 1B

QUALITY MEASURES FOR HAZE

Figure 20T:
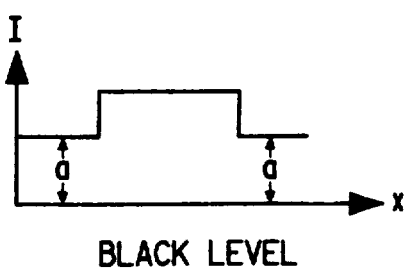

| NAME | EQUATION/OPERATION | GRAPHICAL REPRESENTATION | QUANTIFYABLE PARAMENTERS | COMMENTS |
|---|---|---|---|---|
| *Haze Level | No Equation (DC) level above black | See FIG. 20T. | a = haze level | DC will never be perfectly straight line <br> $<a> = \dfrac{1}{N} \sum_i S_{min}(x_i)$; <br> N = # points summed |

TABLE 1C

QUALITY MEASURES FOR CONTRAST

Figure 20U:
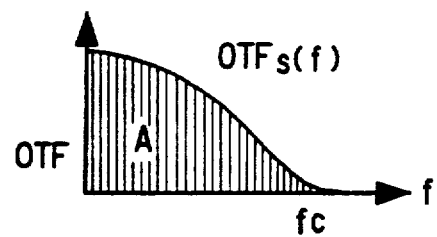

| NAME | EQUATION/OPERATION | GRAPHICAL REPRESENTATION | QUANTIFYABLE PARAMENTERS | COMMENTS |
|---|---|---|---|---|
| *Contrast- $C_o$(optical) Without Haze | $1/K \int_o^{fc} OTF_s(f)df$ <br> where $K = \dfrac{1}{N} \int_{\Delta x} S(x)dx$ | See FIG. 20U. | A | Derived from first principles. $\Delta x$ = width of S(x) transition, N = # points integrated |

TABLE 1C-continued

QUALITY MEASURES FOR CONTRAST

Figure 20V:
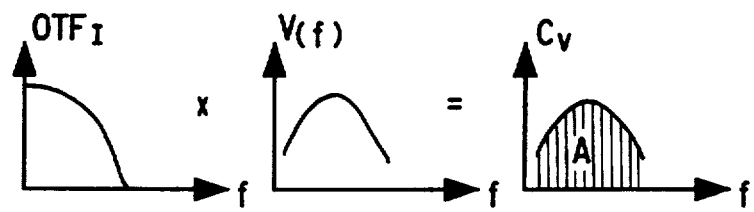
Figure 20W:
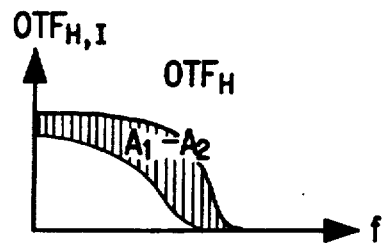
Figure 20X:
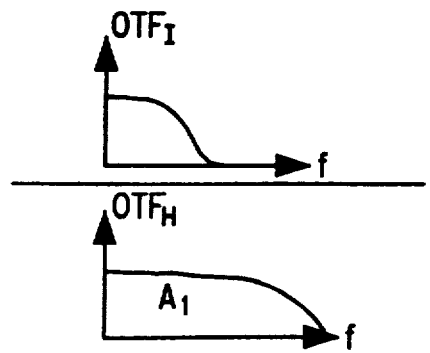
Figure 20Y:
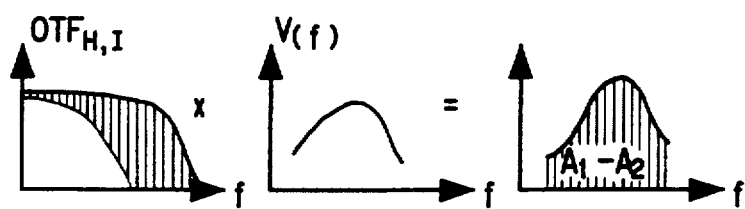
Figure 20Z:
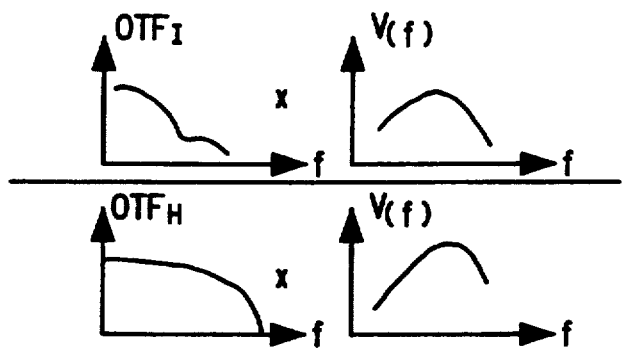

| NAME | EQUATION/OPERATION | GRAPHICAL REPRESENTATION | QUANTIFYABLE PARAMENTERS | COMMENTS |
|---|---|---|---|---|
| *Contrast- $C_v$ (Visual) Without Haze | $1/K \int_0^{fc} OTF_1(f)V(f)df = C_V$ $I = S,P$ | See FIG. 20V. | A | V(f) is in cycles per degree, hence it is a function of distance of viewing. |
| *Contrast $C_h$ With Haze | $C_h \approx C_1(1 - a/K)$ $I = O,V$ | See FIG. 20W. | $C_h, C_O, C_v$, a | This result has also been derived from 1st principles. a = haze level see Table 1B |
| OTF Area Difference | $\int [OTF_H(f) - OTF_1(f)]df$ $I = S,P$ | See FIG. 20X. | $A_1 - A_2$ | Contrast Difference (without haze) |
| OTF Area Ratio | $\int OTF_1(f)df / \int OTF_H(f)df$ $I = S,P$ | | $A_2/A_1$ | Contrast Ratio (without haze) |
| Visually Weighted OFT Area Difference (Visual Contrast Difference) | $\int [OTF(f)_H - OTF_1(f)]V(f)df$ $I = S,P$ | See FIG. 20Y | $A_1 - A_2$ | Visual Contrast Difference (without haze) |
| Visually Weighted OTF Area Ratio (Visual Contrast Ratio) | $\dfrac{\int OTF(f)_1 V(f)df}{\int OTF(f)_H V(f)df}$ $I = S,P$ | See FIG. 20Z. | $A_2/A_1$ | Visual Contrast Ratio (without haze) |

TABLE 1D

QUALITY MEASURES FOR GLOSS

Figure 21A:
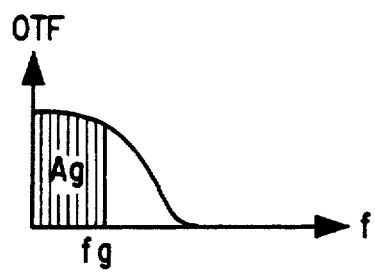
FIGS. 21$a$-$l$ are graphical representations of Quality Measures for Image Quality.
Figure 21B:
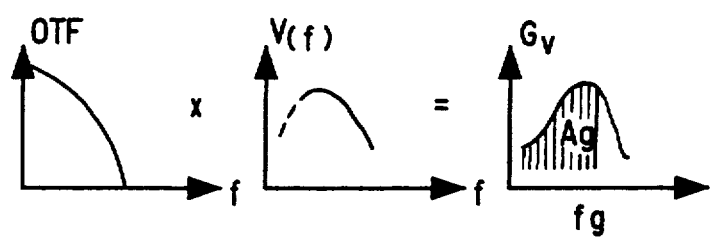

| NAME | EQUATION/OPERATION | GRAPHICAL REPRESENTATION | QUANTIFYABLE PARAMENTERS | COMMENTS |
|---|---|---|---|---|
| *OTF Gloss ($G_o$) (Optical) | $\int_0^{fg} OTF_1(f)df$ | See FIG. 21A. | $G_o = Ag$ | fg is low frequency cutoff which blurrs highlights associated with source image-measured parameter |
| *OTF Gloss ($G_v$) (Visual) | $\int_0^{fg} OTF_1(f)V(f)df$ | See FIG. 21B. | $G_v = A'g$ | Same as above, but includes visual spatial frequency response. |

TABLE 1E

QUALITY MEASURES FOR CLASSICAL GLOSS

Figure 21C:
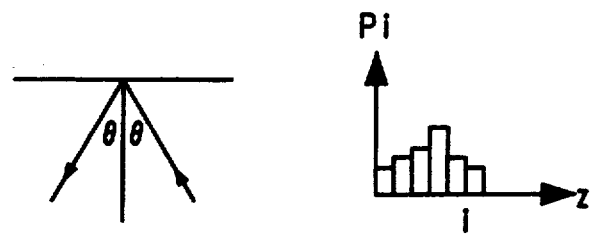
Figure 21D:
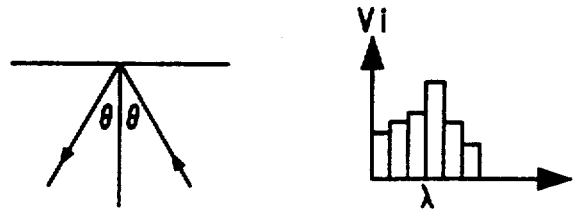

| NAME | EQUATION/OPERATION | GRAPHICAL REPRESENTATION | QUANTIFYABLE PARAMENTERS | COMMENTS |
|---|---|---|---|---|
| *Classical (Optical) Gloss | $\sum_i P_i / BG$ where $BG = \sum_i P_i^{BG}$ | See FIG. 21C. | Total Image intensity relative to BG image intensity; $A/A_{BG}$ | If we make a measurement at an acute angle $\theta$ and sum the data translation histogram values $P_i$ we can get gloss |
| *Classical (Visual) Gloss | Same as above with a visual luminance spectral response $V_\lambda$ at the detector | See FIG. 21D. | Same as above, but with luminance values | Same as above but with luminance values rather than intensity values. |

TABLE 1F

QUALITY MEASURES FOR ORANGE PEEL & MICROWRINKLE

Figure 21E:
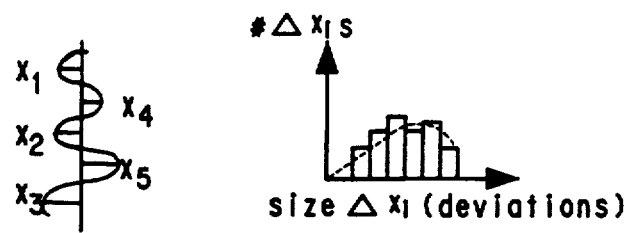
Figure 21F:
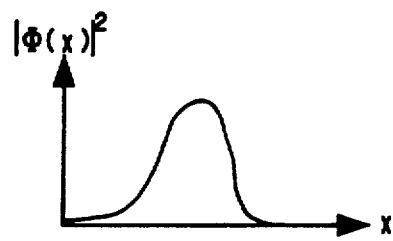
Figure 21G:
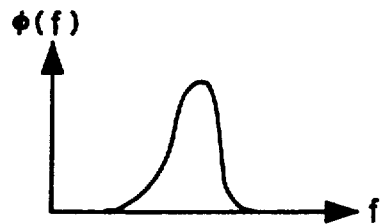
Figure 21H:
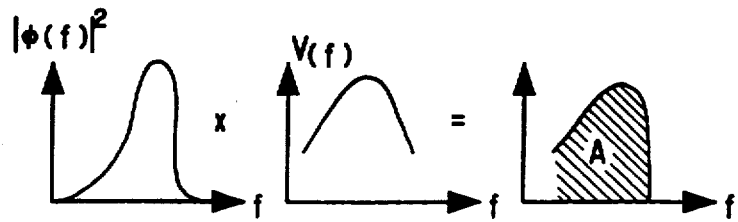

| NAME | EQUATION/OPERATION | GRAPHICAL REPRESENTATION | QUANTIFYABLE PARAMENTERS | COMMENTS |
|---|---|---|---|---|
| *Peel Image Distortion | $\frac{dP(x)}{dx} = 0; x = x_i$<br>i = scan line # | See FIG. 21E. | $h, w, \frac{h}{w}, A$ | Uses histogram, statistical techniques. on deviations $x_i$ to obtain Peel measure |
| *Peel Auto Correlation | $\int \phi(x')\phi(x' + x)dx'$ | See FIG. 21F. | $h, w, \frac{h}{w}, A$ | Measure of the spatial coherence (spatial purity) of the peel signal. Peel and Microwrinkle measure |
| *Fourier Transform Auto Correlation (Peel Frequency Spectrum) | $F.T.\{\phi(x')\phi(x' + x)dx\} = |\phi(f)|^2$ | See FIG. 21G. | $h, w, \frac{h}{w}, A$ | By the Wiener-Khintchine theorem this is the spatial frequency POWER SPECTRUM of the Peel. Peel and Microwrinkle measure |
| Visual Peel Frequency Power Spectrum | $|\phi(f)|^2 \cdot V(f)$ | See FIG. 21H. | H, w, h/w, A | Modifies physical Peel frequencies to those the eye can see. Peel measure |

TABLE 1G

QUALITY MEASURES FOR IMAGE QUALITY

Figure 21I:
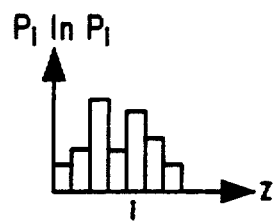

| NAME | EQUATION/OPERATION | GRAPHICAL REPRESENTATION | QUANTIFY-ABLE PARA-MENTERS | COMMENTS |
|---|---|---|---|---|
| *Information Entropy | $E = - \sum_i P_i \ln P_i$<br>and $\sum_i P_i = 1$ | See FIG. 21I. | Area under curve of PinP | Traditional statistical measure of information content. Used in Image Analysis as a measure of Image Quality |
| *Relative Entropy | $E'' = - \sum_i P_i/P_i^{BG}(\ln P_i - \ln P_i^{BG})$<br>or<br>$E'' = E/E^{BG}$ | Same as above. | | Same as above<br>BG = Black Glass Response. |
| Spatial Area | $\int S(x)dx; \int P(x)dx$ | (see Table 1A) | A | DOI Measure (absolute) for (S); Image Quality for (P) |
| Spatial Area Difference | $\int[H(x) - S(x)]dx;$<br>$\int[H(x) - P(x)]dx$ | (see Table 1A) | $A_1 - A_2$ | DOI Measure (relative) for (S); Image Quality for (P) |
| Spatial Area Ratio | $\frac{\int S(x)dx}{\int H(x)dx}; \frac{\int P(x)dx}{\int H(x)dx}$ | (see Table 1A) | $A_2/A_1$ | DOI Measure (relative) for (S); Image quality for (P) |
| Spectral Area (Amplitude) | $\int \bar{s}(f)df; \int \bar{p}(f)df$ | (see Table 1A) | A | DOI measure (absolute) for (S); Image Quality for (P) |
| Spectral Area Difference (Amplitude) | $\int[h(f) - \bar{s}(f)]df$<br>$\int[h(f) - \bar{p}(f)]df$ | (see Table 1A) | $A_1 - A_2$ | DOI measure (relative) for (S); Image Quality for (P) |
| Spectral Area ratio (Amplitude) | $\frac{\int \bar{s}(d)df}{\int h(f)df}; \frac{\int \bar{p}(f)df}{\int h(f)df}$ | (see Table 1A) | $A_2/A_1$ | DOI measure (relative) for (S); Image Quality measure for (P) |
| Visually Weighted Spectral Area (Amplitude) | $\int \bar{s}(f)V(f)df;$<br>$\int \bar{p}(f)V(f)df$ | (see Table 1A) | A | DOI Measure for (S); Image Quality measure for (P) |
| *Visually Weighted Spectral Area Difference | $\int[h(f) - \bar{s}(f)]V(f)df$<br>$\int[h(f) - \bar{p}(f)]V(f)df$ | (see Table 1A) | $A_1 - A_2$ | DOI measure for (S); Image Quality for (P) |

TABLE 1G-continued

QUALITY MEASURES FOR IMAGE QUALITY

Figure 21J:
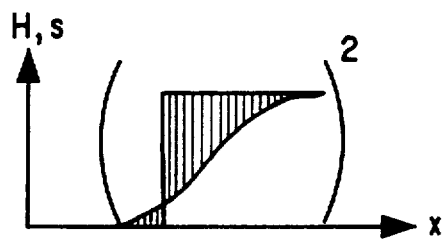
Figure 21K:
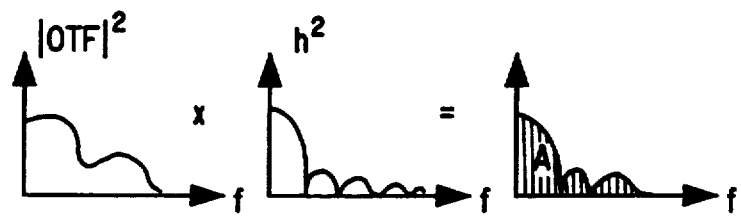
Figure 21L:
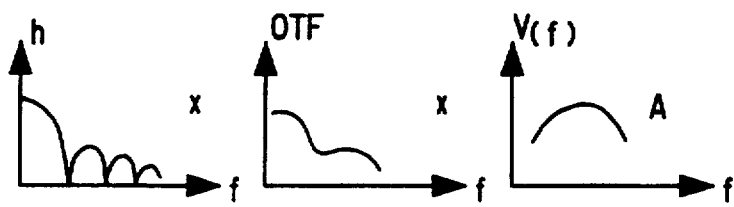

| NAME | EQUATION/OPERATION | GRAPHICAL REPRESENTATION | QUANTIFY-ABLE PARA-MENTERS | COMMENTS |
|---|---|---|---|---|
| (Amplitude) | | | | |
| Visually Weighted Spectral Area Ratio (Amplitude) | $\dfrac{\int s(f)V(f)df}{\int h(f)V(f)df}$ ; $\dfrac{\int p(f)V(f)df}{\int h(f)V(f)df}$ | (see Table 1A) | $A_2/A_1$ | DOI measure (re;atove) for (S); Image Quality measure for (P) |
| Linfoot[2] Image Quality Measures: Mean Square Error MSE | $\int [H(x) - S(x)]^2 dx$ | See FIG. 21J. | $(A_1 - A_2)^2$ | The Linfoot Group is often used in photography as a measure of Image Quality (DOI measure) |
| Linfoot: Fidelity | $\dfrac{1}{K'} \int 1 - |1 - OTF(f)|^2 |h(f)|^2 df$ where $K' = \int |h(f)|^2 df$ | See FIG. 21K | (1-MSE) | Unity minus the mean squared error measures DOI, Image Quality |
| Linfoot: Relative Srructural Content: | $\dfrac{1}{K'} \int |OTF(F)|^2 |h(f)|^2 df$ | | A | Same as Bell Systems Weight Power. Not clear what this "measures" |
| Linfoot: Correllation | $\dfrac{1}{K'} \int OTF(f) |h(f)|^2 df$ | | A | All other Linfoot "OTF" measures of Image Quality are simplified examples of this and the above three. Measures DOI, Image Quality? |
| Linear Spatial Visual Response ($Q_1$) | $\dfrac{1}{K_1} \int h(f)OTF(f)V(f)df$ where $K_1 = \int h(f)OTF(f)_{BG}V(f)df$ | See FIG. 21L. | A | Spatial analogy (isomorphism) to colorimetric Y calculation for luminance Value depends on position "z" |
| *Power Law Spatial Visual Response ($Q_2$) | $1/K_2 \int (h(f)OTF(f))^\gamma V(f)df$ where $K_2 = \int (h(f)OTF(f)_{BG})^\gamma V(f)df$ $\gamma$ determined empirically | | $A^\gamma$ | Cornsweet claims the visual spatial response is to a nonlinear stimulus Value depends on position "z". Also useful as a measure of DOI (absolute) |
| log Spatial Visual Response ($Q_3$) | $1/K_3 \int \log(h(f)OTF(f))V(f)df$ where: $K_3 = \int \log(h(f)OTF(f)_{BG})V(f)df$ | | log A | Different form of Cornsweet Nonlinearity Value depends on position "z" |
| Granger 1/f smoothed Response ($Q_4$) | $1/K_4 \int h(\kappa)OTF(\kappa)V(\kappa)d\kappa$ where: $K_4 = \int h(\kappa)OTF(\kappa)_{BG}V(\kappa)d\kappa$ $\kappa = \ln f$ | | $A_{\log f}$ | Granger claims 1/f → ln f smooths neural processes in vision |
| Nonlinear Q Values Color Theory (Power Law) | $Q'_I = (Q_I)^\gamma$ $I = 1,2,3,4$ | | | Analogous to Cube-Root color theory i.e. $L = 25Y^{\frac{1}{3}} - 16$, etc |
| Nonlinear Q Values analogous to Color Theory (Weber's Law) | $Q'_I = \kappa \log Q_I$ $I = 1,2,3,4$ | | | Weber-Fechner "Log" law is a standard nonlinear form in Psychology and Psychophysics |

[2]E. H. Linfoot. "Fourier Methods in Optical Image Evaluation" Focal Press, London (1964)

In accordance with the above, the method of the invention includes generating a spatially coherent and uniform collimated beam 19 of polychromatic light which is directed through mask 21 onto surface 22 of test panel 23 at an angle of incidence θ. Detector 26 senses the specularly reflected image of a portion of the mask 21, and moves through a preselected sequence of focal planes 32, normal to the optic axis 33 thereof, and measures the intensities of the preselected points in the scanned image of mask 21 at each focal plane in the sequence. Computer 36 calculates the required Fourier spectra from the measured intensity values obtained at each focal plane and therefrom generates a "T(z) curve" similar to the one displayed in FIG. 16. Experience teaches us that the relevant appearance attributes always occur at the maxima and minima, and in the same sequence, along this curve. Thus, standard methods of elementary $\{z_o\}$ values of the aforementioned extrema and position the detector 26 at such locations. This procedure is known as "accommodation" and is similar in function to the process used by the eye-brain system in vision for the same purpose. The absence of any such peak on the T(z) curve indicates that this particular appearance attribute is not present on the surface 22 of test panel 23.

The accommodation procedure as just explained is invoked to position detector 26 at the extrema locations $\{z_o\}$. Then, the information associated with the image intensity values, $I^oj(x,zo)$, at these focal positions, $z_o$, are manipulated in accordance with the algorithms and prescriptions relevant to the detected appearance feature at $z_o$, as provided in Tables 1A–1G. The quality measures so derived are further standardized with the imaging characteristics of a perfect reflector, such as a mirror or black glass. It is apparent from Tables 1A–1G that the three modeling phases associated with the isomorphism between color vision and spatial vision, including the elementary appearances measures, $A^k(z)$, and the perceptual attributes $F(A^k(z))$, are utilized where applicable. The optical transfer function, (OTF), has a predominant role in many of these calculations but, conventional image processing algorithms, known in the art, are also employed for completeness.

In the above methods, although the calculations relating to the detection of the particular focal plane positions, $\{z_o\}$, that correspond to the surface features of interest, and the mathematical determinations of surface attributes, are performed subsequent to detector 26 travel through the entire sequence of all focal planes along the "z" axis, it is within the scope of this invention to carry out all calculations at each focal position, while and during detector 26 movement relative to panel 23, to determine the appearance features of the surface 22.

MEASUREMENT PROCEDURE

Figure 17:
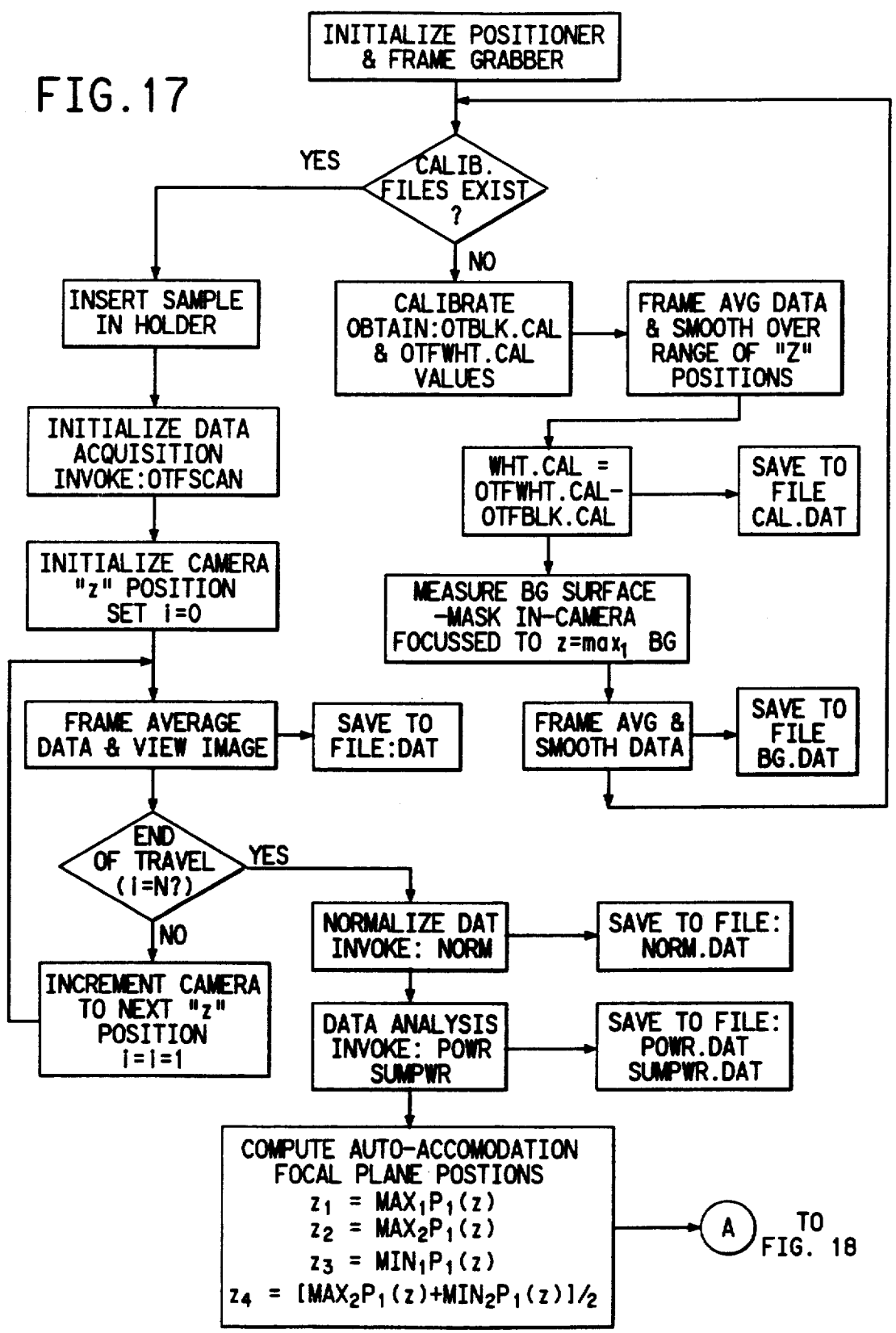
FIGS. 17-18 are flow charts of the measurement algorithms of the present invention.
Figure 18:
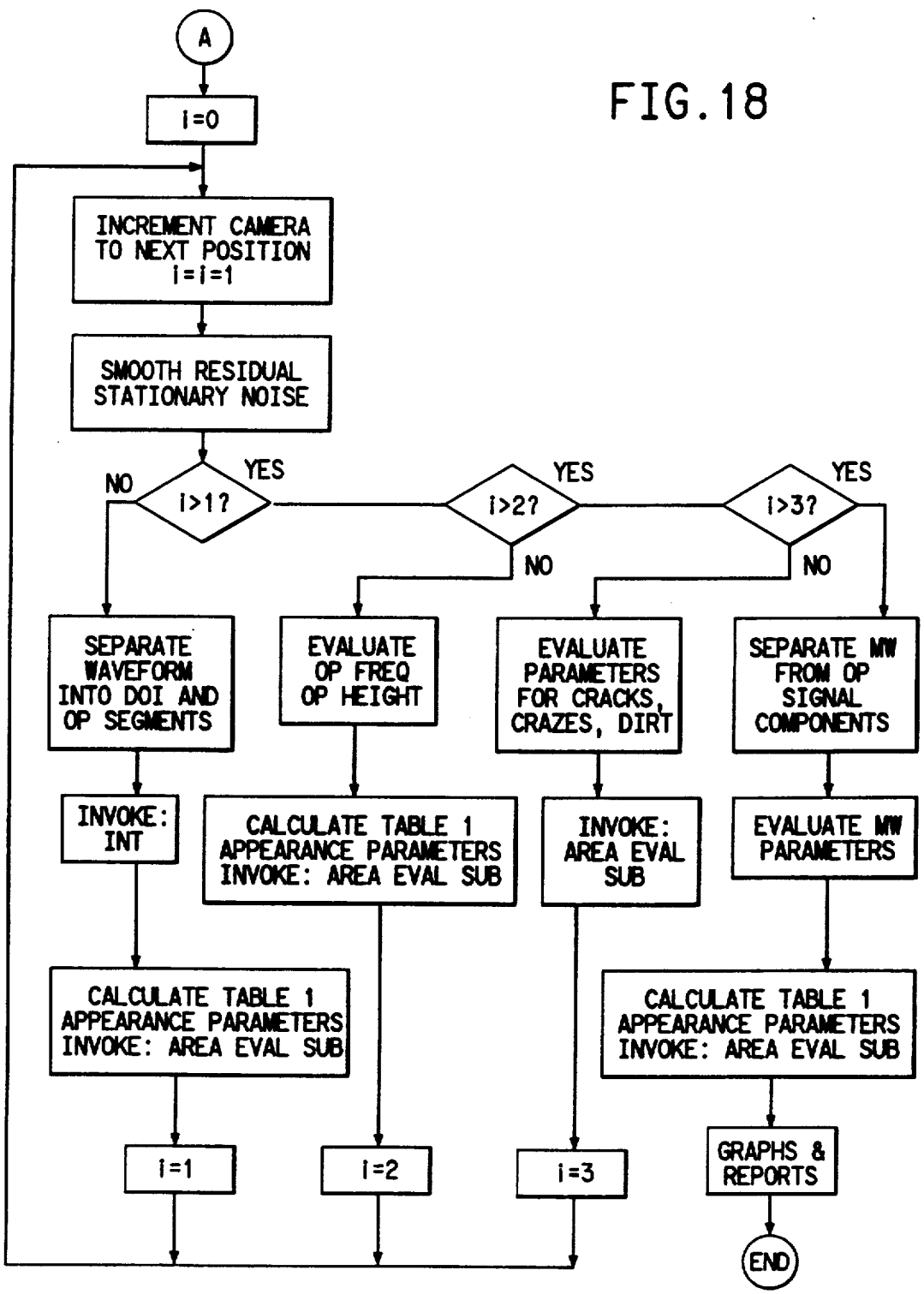

FIGS. 17–18 are flow charts outlining the measurement steps that include calibration, scan data acquisition, data normalization, data analysis, and graphical/reporting output functions. In the procedure provided below, various descriptive file names/routines have been used for illustration purpose only. One of ordinary skill in the art would be aware that other file names/routines may also be used without departing from the spirit of the invention. To calibrate the instrument, the operator turns off light source 10 and removes any test panel from holder 24 to obtain and save in file OTFBLK.CAL camera black-level scan values. Next, a black glass reference panel is inserted and the source 10 is turned back on to measure the white level reference spatial uniformity with the edge target mask 21 removed from beam 19 and the camera 26 translated over its full range of "z" positions, typically 0 to 4 inches. This procedure measures the full field upper light level reference and after smoothing, the data is saved in file OTFWHT.CAL. The difference between the two data sets, WHT.CAL, is also saved in the file. Similarly, the instrument spatial response function is obtained by measuring the black glass reflectance in the same manner as the white calibration, but with the mask 21 in place and the detector translated to that "z" position which yields the best DOI reading.

The scan data acquisition phase begins by inserting a sample surface to be measured into the holder and invoking the OTFSCAN measurement routine which automatically scans the sample, computes, measures, and displays the results. The routine operates as follows:

At the end of the camera's travel through the "z" positions, a data normalization subroutine, NORM is performed to (1) correct for any non-uniformity in the illumination of the surface due to geometric distortion in the optical system. This is done by subtracting the corresponding pixel values of the camera black level OTFBLK.CAL, from the test panel data (DAT) and then dividing this result by the difference between the white reference, OTFWHT.CAL and black reference OTFBLK.CAL; (2) smooth the scan data using a novel filtering algorithm that eliminates camera and A/D converter noise without affecting the edge transition frequency content; (3) center the series of pulse waveforms to the same x-raster value to correct for any shift in the images which may occur with slight misalignment of the optical system and/or distortion as it is translated in the "z" direction; and (4) standardize the centered waveform data from (3) using BG.DAT as a reference for the maximum and minimum amplitude values of all remaining measured signals.

This step facilitates comparison of panels with different lightness levels, haze levels, gloss levels, etc.

The data analysis phase is initiated next using POWR and SUMPWR routines. POWR computes the Fast Fourier transform of the NORM.DAT scan data and the log power spectra of $P^oj(f,z)$ from the "windowed" results, i.e., the results obtained by using a mask with a slit, in accordance with equations (1) and (4). Since windowing produces effects which tend to overemphasize the low spatial frequency information, taking the logarithm of $P^oj(f,z)$ partially compensates for the effect by emphasizing the high spatial frequency information over the low frequency information.

Figure 16:
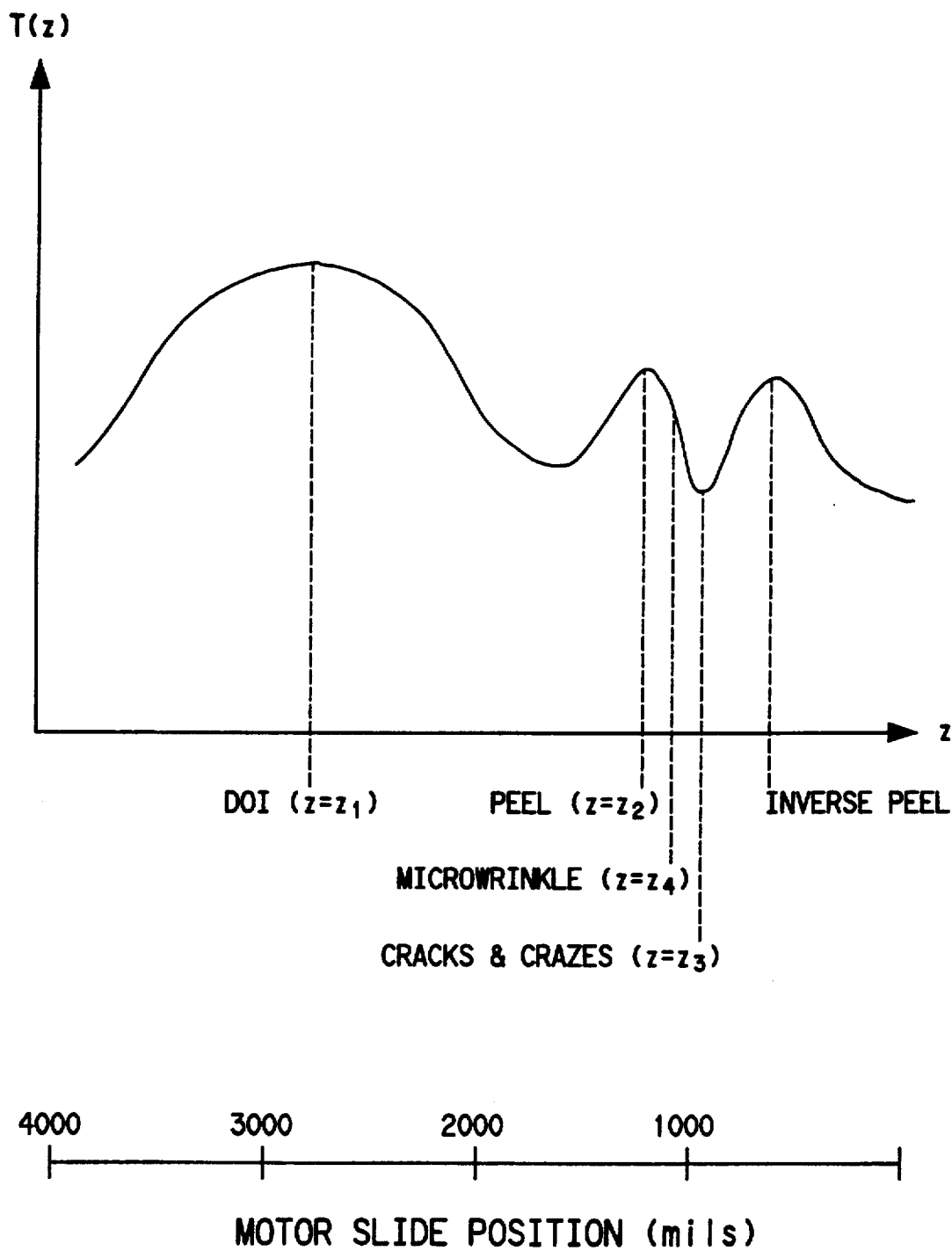
FIG. 16 is a graphic illustration of the total integrated Fourier frequency power function, $T(z)$.

The logarithmically weighted Fourier transform power spectrum, POWR, is averaged and then integrated over spatial frequency space in accordance with equations (2) and (5) respectively, using SUMPWR to obtain total reflected image power T(z) at a distance "z" of the imager 26 along the optic axis 54 from the surface 22 of the test panel 23. FIG. 16 is a typical graph of T(z) for a painted panel.

The auto-accommodation routine is a coincidental way to adjust the focal plane 32 of the imager 26 to ™ best foous" positions to measure distinctness of image $(z=z_1)$, orange peel $(z=z_2)$, microwrinkle $(z=z4)$, and cracks and crazes $(z=z3)$. Although the procedure may be applied "on the fly", i.e., while the detector 26 is moving, by determining extreme values of T(z) as they occur in the course of computing this function at the end of each increment of travel in the "z" direction, a more exact, but slower, method is to wait for normalization of all data after the "z" scan is complete, locate all the extrema in "z" coordinates, and then go back to the focal planes of importance for computation of the associated appearance parameters listed in Table 1. The latter method is that outlined in the flow chart, FIGS. 17–18.

The procedure described earlier is applied to separate the S transition from the P signal components before DOI and OP appearance values are obtained. Equivalently, the separation can be accomplished at the derivative level, i.e. $I^1j(x,z)$.

Since the appearance measures listed in Table I represent the utilization of measured data from only one "y" scan line at a time, two dimensional area evaluation algorithms may be invoked to gain an areal assessment of appearance parameters that are important over some area of view on the test panel surface.

In order to accomplish this, we consider the array of pixel values in each image as a two dimensional function $I^o(x,y)$ and restate the equations in Table 1 accordingly, for example:

$$\text{optical contrast} = 1/K \int \int OTF_s(f_x,f_y) df_x df_y \text{ (without haze)}$$

$$\text{where } K = \frac{1}{N^2} \int \int S(x,y) dx dy$$

Currently, a two-dimensional analog for $V(f)$, the visual spatial frequency response, is not yet available so that the associated 2-D visual appearance parameters cannot be computed.

An alternate to the 2-D method outlined above is to prepare a histogram of the values for each parameter in Table 1 computed for a selected set of scan lines so that a statistical distribution can be fit to the data. In this way, the mean, variance, height to width ratio and area under the curve so derived can be used to measure the variation in each appearance parameter under question as a function of areal surface changes.

A number of graphing and data analysis routines may be invoked, and several examples are mentioned here in the following paragraphs:

(a) PLOTM—for graphing data generated by the data acquisition phase, including normalized data plus POWR, SUMPWR, and INT data sets.

(b) OTFMOV—for enabling the user to position the camera anywhere in the direction of motion along the optic axis in order to visually find the "best focus" for the features viewed (e.g., slit image, OP, MW, etc.)

(c) AMPL—similar to POWR, but for computing the Fourier transform amplitude spectrum (amplitude density function), i.e., the square root of the Fourier power spectrum.

(d) SUMAMP—similar to SUMPWR but for integrating the amplitude density spectrum obtained from AMPL.

(e) DERIV—for computing the derivative of any measured or derived data set.

(f) FFT—for computing one-dimensional Fourier transform of the records in a data file, providing data on both real and imaginary parts.

(g) THREED—for generating a three-dimensional plot of the data as a function of intensity values stored from the results of any "y" and "z", or any "x" or "y" sequence of scans (FIGS. 12-15).

With the method and instrument capability of this invention, it is probable that the techniques of fractal analysis and fractal dimension computations can also be used to develop practical non-visual appearance scales that will satisfy many appearance requirements that are not visually oriented.

While this invention has been described as having a preferred design, it will be understood that it is capable of further modifications, uses and/or adaptations that follow in general the principle of the invention, including such departures from the present disclosure as come within the known or customary practice in the art to which the art pertains and, as may be applied to the central features hereinbefore set forth, and fall within the scope of the invention or limits of the claims appended hereto.

What is claimed is:

1. A method for measuring the appearance features of a surface, comprising:
    (a) generating a spatially coherent and uniform collimated beam of polychromatic light;
    (b) interposing a beam limiting means into said beam of polychromatic light;
    (c) directing said beam of polychromatic light, spatially filtered by said beam limiting means, onto a surface at an angle of incidence;
    (d) detecting and scanning the specularly reflected image of a portion of said beam limiting means with a scanned imaging detector;
    (e) translating the detector along the optic axis through a sequence of spatially distinct focal planes normal to the optic axis, including focal planes corresponding to said surface and to said beam limiting means;
    (f) measuring surface reflectance from a plurality of preselected points in each one of said sequence of scanned detected focal plane images;
    (g) transforming said reflectances into a corresponding sequence of focal plane spatial frequency spectra;
    (h) selecting focal plane spectral data according to the occurance of maximum and minimum signatures in the power spectra of said focal plane sequence;
    (i) standardizing said spectral data with the spatial frequency characteristics of a perfect reflecting surface;
    (j) calculating from said standardized measurements, the optical transfer function (OTF), spatial frequency response, power, and amplitude spectra and in conjunction with the visual spatial frequency response characteristic $V(f)$ and standard psychophysical methodology, mathematically determine the appearance attributes of said surface.

2. The method of claim 1, wherein the surface appearance attributes are defined by quality measures of: orange peel frequency, orange peel amplitude, microwrinkle, cracks and crazes, distinctness of image, gloss, haze, contrast, luster, fog, and texture.

3. The method of claim 1, wherein calculating specific appearance attributes includes the steps:
    (a) Weighting the spectral distribution function, $F^k(f,z)$ with the visual spatial frequency response function, $V(f)$;
    (b) determining elementary appearance measures, $A^k(z)$, in accordance with:

$$A^k(z) = \int F^k(f,z) V(f) df;$$

(c) transforming the functions $A^k(z)$ with algorithms selected from tabulated functions defining quality measures to obtain perceived values of said appearance attributes.

4. The method of claim 1 wherein selecting said sequence of focal plane positions and spectral data corresponding thereto is based upon the following steps:
    (a) integrating the Fourier power spectra derived from the scanned and measured intensity values obtained at each of said focal planes in the sequence in accordance with the following equation:

$$T(z) = \int \log [P^0(f,z) + 1] df;$$

(b) determining the extrema as a function of displacement along the optic axis;
(c) positioning the detector according to extrema location.

5. The method of claim 1 including the step of standardizing the spectral data with the spectral reflectance of black glass.

6. The method of claim 1 including the step of directing said beam of spatially filtered polychormatic light onto the surface at a normal angle of incidence.

7. The method of claim 1 including the step of directing said beam of spatially filtered polychromatic light onto the surface at an acute angle of incidence ranging from about 0° to about 50°.

8. A method of measuring the appearance features of a surface, comprising:
   (a) generating a spatially coherent and uniform collimated beam of polychromatic light;
   (b) interposing a beam limiting means into said beam of polychromatic light;
   (c) directing said beam of polychromatic light, spatially filtered by said beam limiting means, onto a surface at an angle of incidence;
   (d) detecting and scanning the specularly reflected image of a portion of said beam limiting means with a scanned imaging detector;
   (e) positioning the focal plane of said detector at a first position normal to the ptic axis thereof;
   (f) measuring the surface reflectance from a plurality of preselected points in the scanned focal plane image;
   (g) transforming said reflectance values to obtain spatial frequency spectra;
   (h) standardizing said spectral data with the spatial frequency characteristics of a perfect reflecting surface;
   (i) calculating from said standardized measurements, power and amplitude spectra;
   (j) integrating said power spectra to obtain T(z) values to determine the existence of extrema;
   (k) adjusting the focal plane position of said detector to obtain the extrema positions corresponding to the appearance feature sought;
   (l) calculating from said standardized measurements, the optical transfer function (OTF), spatial frequency response, power and amplitude spectra and in conjunction with the visual spatial frequency response characteristic V(f) and standard psychophysical methodology, mathematically determine the appearance attributes of the surface dependent upon the spatial frequency feature measured at said focal plane extrema positions.

9. The method of claim 8, further including the steps of:
   (a) repositioning said detector at a second focal plane position;
   (b) repeating steps (f) through (l) to mathematically determine the appearance attributes dependent upon the spatial frequency feature measured at said second focal plane position.

10. The method of claim 8 or claim 9 wherein the surface appearance attributes are defined by quality measures of: orange peel frequency, orange peel amplitude, distinctness of image, gloss, haze, contrast, microwrinkle, texture, luster, fog, and cracks and crazes.

11. The method of claim 8 or claim 9, wherein calculating specific appearance attributes include the steps:
   (a) weighting the spectral distribution function $F^k(f,z)$, with the visual spatial frequency response function, $V(f)$;
   (b) determining elementary appearance measures, $A^k(z)$, in accordance with:

$$A^k(z) = \int F^k(f,z) V(f) df;$$

(c) transforming the functions $A^k(z)$ with algorithms selected from tabulated functions defining quality measures to obtain perceived values of said appearance attributes.

12. The method of claim 8 or claim 9 wherein the integrating step includes the use of the equation:

$$T(z) = \int \log[P^0(i\ f,z)+1] df$$

13. The method of claim 8 or claim 9 including the step of standardizing the spectral data with the spectral reflectance of black glass.

14. The method of claim 8 or claim 9 including the step of directing said beam of spatially filtered polychromatic light onto the surface at a normal angle of incidence.

15. The method of claim 8 or claim 9 including the step of directing said beam of spatially filtered polychromatic light onto the surface at an acute angle of incidence ranging from about 0° to about 50°.

16. An apparatus for measuring the appearance features of a surface, comprising:
   (a) a source for generating a spatially coherent and uniform collimated beam of polychromatic light;
   (b) means for holding the surface flat;
   (c) beam limiting means for spatially filtering said beam of polychromatic light to be interposed between said source and the surface;
   (d) detector means for receiving the specularly reflected image of a portion of said beam limiting means from the surface;
   (e) means for translating said detector means relative to the surface along the optic axis.

17. The apparatus of claim 16, wherein:
   (a) said beam limiting means includes an optical mask with a slit.

18. The apparatus of claim 16, wherein:
   (a) said beam limiting means is selected from geometries comprising step, pulse, polar, semi-polar, Ronchi Ruling and grid masks, respectively.

19. The apparatus of claim 16, and including:
   (a) means for processing information sensed by said detector means.

20. The apparatus of claim 16, wherein:
   (a) said beam generating means is positioned so as to direct the beam onto said surface at an acute angle of incidence ranging from about 0 to about 50.

21. The apparatus of claim 16, wherein:
   (a) said beam generating means is positioned so as to direct the beam onto said surface at a normal angle of incidence.

22. The apparatus of claim 21, and
   (a) beam splitter means positioned between said source and said surface.

23. The apparatus of claim 16, wherein:
   (a) said detector means comprises a scanned imaging detector.

24. The apparatus of claim 23, wherein:
   (a) said detector is a charged coupled camera.

25. The apparatus of claim 19, wherein:
   (a) said information processing means includes means for generating a three-dimensional image.

26. The apparatus of claim 19 and including:
   (a) auto-accommodation means for adjusting the focal plane of said detector means to at least one detected image that corresponds with the predetermined image of a surface feature.

* * * * *